(12) United States Patent
Borden et al.

(10) Patent No.: US 7,465,591 B2
(45) Date of Patent: *Dec. 16, 2008

(54) EVALUATING A GEOMETRIC OR MATERIAL PROPERTY OF A MULTILAYERED STRUCTURE

(75) Inventors: Peter G Borden, San Mateo, CA (US); Jiping Li, Fremont, CA (US)

(73) Assignee: Applied Materials, Inc., Santa Clara, CA (US)

( * ) Notice: Subject to any disclaimer, the term of this patent is extended or adjusted under 35 U.S.C. 154(b) by 414 days.

This patent is subject to a terminal disclaimer.

(21) Appl. No.: 10/977,380

(22) Filed: Oct. 29, 2004

(65) Prior Publication Data

US 2005/0088188 A1    Apr. 28, 2005

Related U.S. Application Data

(63) Continuation of application No. 09/521,232, filed on Mar. 8, 2000, now Pat. No. 6,812,047.

(51) Int. Cl.
*H01L 21/00* (2006.01)
*G01J 4/00* (2006.01)

(52) U.S. Cl. ......................... 438/16; 356/369

(58) Field of Classification Search .................. 438/16; 356/369

See application file for complete search history.

(56) References Cited

U.S. PATENT DOCUMENTS

| | | | |
|---|---|---|---|
| 3,462,602 A | 8/1969 | Apple | 250/83 |
| 3,803,413 A | 4/1974 | Vanzetti et al. | 250/338 |
| 3,909,602 A | 9/1975 | Mioka | 235/151.3 |
| 3,930,730 A | 1/1976 | Laurens et al. | 356/106 |
| 4,201,087 A | 5/1980 | Akita et al. | 73/339 |

(Continued)

FOREIGN PATENT DOCUMENTS

| | | | |
|---|---|---|---|
| EP | 0 622 624 A1 | * | 11/1994 |
| EP | 0 718 595 | | 6/1996 |
| JP | 05006929 A | | 1/1993 |
| JP | 2000009443 A | | 1/2000 |
| WO | WO 97/08536 | | 3/1997 |
| WO | WO 99/64880 | | 12/1999 |

OTHER PUBLICATIONS

J. Opsal, "High Resolution Thermal Wave Measurements and Imaging of Defects and Damage in Electronic Materials" Photoacoustic and Photothermal Phenomena II, Springer Series in Optical Sciences, vol. 62, Springer Verlag Berlin, Heidelberg, 1990.

(Continued)

*Primary Examiner*—Evan Pert
(74) *Attorney, Agent, or Firm*—Omkar Suryadevara

(57) ABSTRACT

A structure having a number of traces passing through a region is evaluated by using a beam of electromagnetic radiation to illuminate the region, and generating an electrical signal that indicates an attribute of a portion (also called "reflected portion") of the beam reflected from the region. The just-described acts of "illuminating" and "generating" are repeated in another region, followed by a comparison of the generated signals to identify variation of a property between the two regions. Such measurements can identify variations in material properties (or dimensions) between different regions in a single semiconductor wafer of the type used in fabrication of integrated circuit dice, or even between multiple such wafers. In one embodiment, the traces are each substantially parallel to and adjacent to the other, and the beam has wavelength greater than or equal to a pitch between at least two of the traces. In one implementation the beam is polarized, and can be used in several ways, including, e.g., orienting the beam so that the beam is polarized in a direction parallel to, perpendicular to, or at 45° to the traces. Energy polarized parallel to the traces is reflected by the traces, whereas energy polarized perpendicular to the traces passes between the traces and is reflected from underneath the traces. Measurements of the reflected light provide an indication of changes in properties of a wafer during a fabrication process.

39 Claims, 13 Drawing Sheets

U.S. PATENT DOCUMENTS

| | | | | |
|---|---|---|---|---|
| 4,211,488 | A | 7/1980 | Kleinknecht | 356/433 |
| 4,243,327 | A | 1/1981 | Frosch et al. | 356/432 |
| 4,255,971 | A | 3/1981 | Rosencwaig | 73/606 |
| 4,273,421 | A | 6/1981 | Gurtler | 356/432 |
| 4,455,741 | A | 6/1984 | Kolodner | 29/574 |
| 4,466,748 | A | 8/1984 | Needham | 374/129 |
| 4,468,136 | A | 8/1984 | Murphy et al. | 374/45 |
| 4,521,118 | A | 6/1985 | Rosencwaig | 374/5 |
| 4,522,510 | A | 6/1985 | Rosencwaig | 374/7 |
| 4,579,463 | A | 4/1986 | Rosencwaig et al. | 374/57 |
| 4,632,561 | A | 12/1986 | Rosencwaig et al. | 356/432 |
| 4,634,290 | A | 1/1987 | Rosencwaig | 374/5 |
| 4,636,088 | A | 1/1987 | Rosencwaig et al. | 374/5 |
| 4,710,030 | A | 12/1987 | Tauc et al. | 356/445 |
| 4,750,822 | A | 6/1988 | Rosencwaig et al. | 356/445 |
| 4,795,260 | A | 1/1989 | Schuur et al. | 356/400 |
| 4,854,710 | A | 8/1989 | Opsal et al. | 356/432 |
| 4,950,990 | A | 8/1990 | Moulder et al. | 324/224 |
| 4,952,063 | A | 8/1990 | Opsal et al. | 356/432 |
| 4,975,141 | A | 12/1990 | Greco et al. | 156/626 |
| 4,996,659 | A | 2/1991 | Yamaguchi et al. | 364/579 |
| 5,042,951 | A | 8/1991 | Gold et al. | 356/369 |
| 5,042,952 | A | 8/1991 | Opsal et al. | 356/432 |
| 5,074,669 | A | 12/1991 | Opsal | 356/447 |
| 5,128,864 | A | 7/1992 | Waggener et al. | 364/413 |
| 5,149,978 | A | 9/1992 | Opsal et al. | 250/234 |
| 5,159,412 | A | 10/1992 | Willenborg et al. | 356/445 |
| 5,181,080 | A | 1/1993 | Fanton et al. | 356/381 |
| 5,228,776 | A | 7/1993 | Smith et al. | 374/5 |
| 5,304,931 | A | 4/1994 | Flamig et al. | 324/309 |
| 5,333,050 | A * | 7/1994 | Nose et al. | 356/490 |
| 5,377,006 | A | 12/1994 | Nakata | 356/349 |
| 5,379,109 | A | 1/1995 | Gaskill et al. | 356/445 |
| 5,408,327 | A | 4/1995 | Geiler et al. | 356/432 |
| 5,430,548 | A | 7/1995 | Hiroi et al. | 356/394 |
| 5,454,004 | A | 9/1995 | Leger | 372/99 |
| 5,574,562 | A | 11/1996 | Fishman et al. | 356/432 |
| 5,610,392 | A * | 3/1997 | Nagayama et al. | 250/226 |
| 5,631,171 | A * | 5/1997 | Sandstrom et al. | 436/518 |
| 5,652,716 | A | 7/1997 | Battersby | 364/578 |
| 5,657,754 | A | 8/1997 | Rosencwaig | 128/633 |
| 5,667,300 | A | 9/1997 | Mandelis et al. | 374/43 |
| 5,706,094 | A | 1/1998 | Maris | 356/432 |
| 5,741,614 | A | 4/1998 | McCoy et al. | 430/30 |
| 5,761,082 | A | 6/1998 | Miura-Mattausch | 364/490 |
| 5,764,363 | A | 6/1998 | Ooki et al. | 356/364 |
| 5,790,251 | A | 8/1998 | Hagiwara | 356/351 |
| 5,877,860 | A | 3/1999 | Borden | 356/376 |
| 5,883,518 | A | 3/1999 | Borden | 324/752 |
| 5,966,019 | A | 10/1999 | Borden | 324/752 |
| 5,978,074 | A | 11/1999 | Opsal et al. | 356/72 |
| 6,020,964 | A | 2/2000 | Loopstra et al. | 356/500 |
| 6,049,220 | A | 4/2000 | Borden et al. | 324/765 |
| 6,054,868 | A | 4/2000 | Borden et al. | 324/765 |
| 6,081,334 | A | 6/2000 | Grimbergen et al. | 356/357 |
| 6,118,533 | A | 9/2000 | Banet et al. | 356/345 |
| 6,154,280 | A | 11/2000 | Borden | 356/376 |
| 6,169,601 | B1 | 1/2001 | Eremin et al. | 356/240 |
| 6,178,020 | B1 | 1/2001 | Schultz et al. | 359/107 |
| 6,243,199 | B1 | 6/2001 | Hansen et al. | 359/486 |
| 6,281,027 | B1 | 8/2001 | Wei et al. | 438/14 |
| 6,323,951 | B1 | 11/2001 | Borden et al. | 356/502 |
| 6,327,035 | B1 | 12/2001 | Li et al. | 356/432 |
| 6,330,361 | B1 | 12/2001 | Mitchell et al. | 382/211 |
| 6,336,969 | B1 | 1/2002 | Yamaguchi et al. | 117/7 |
| 6,395,563 | B1 | 5/2002 | Eriguchi | 438/7 |
| 6,400,454 | B1 | 6/2002 | Noguchi et al. | 356/237 |
| 6,426,644 | B1 | 7/2002 | Borden et al. | 324/765 |
| 6,483,594 | B2 | 11/2002 | Borden et al. | 356/502 |
| 6,486,965 | B1 | 11/2002 | Kim | 356/626 |
| 6,489,624 | B1 | 12/2002 | Ushio et al. | 250/559 |
| 6,489,801 | B1 | 12/2002 | Borden et al. | 324/766 |
| 6,525,818 | B1 | 2/2003 | Yin et al. | 356/400 |
| 6,528,333 | B1 | 3/2003 | Jun et al. | 438/16 |
| 6,559,942 | B2 | 5/2003 | Hsieh et al. | 356/369 |
| 6,812,047 | B1 * | 11/2004 | Borden et al. | 438/16 |
| 6,958,814 | B2 * | 10/2005 | Borden et al. | 356/432 |
| 2001/0015937 | A1 | 8/2001 | Yamaguchi et al. | 369/13 |
| 2002/0126732 | A1 | 9/2002 | Shakouri et al. | 374/130 |
| 2002/0186045 | A1 | 12/2002 | Cox | 326/41 |
| 2003/0036231 | A1 | 2/2003 | Bhattacharva et al. | 438/201 |
| 2003/0096436 | A1 | 5/2003 | Satya et al. | 438/11 |
| 2003/0155927 | A1 | 8/2003 | Pinto et al. | 324/11 |

OTHER PUBLICATIONS

A. Rosencwaig, "Thermal Wave Measurement of Thin-Film Thickness", 1986 American Chemical Society, pp. 182-191.

"Thin-Film Thickness Measurements with Thermal Waves", Journal De Physique, Oct. 1983, pp. C6-483-C6-489.

W. L. Smith et al. "Thermal-wave Measurements and Monitoring of TaSIx Silicide Film Properties" J. Vac. Technol.B2(4), Oct.-Dec. 1984, pp. 710-713.

A. Salnick et al., "Nonlinear Fundamental Photothermal Response in 3D Geometry: Experimental Results for Tungsten", (believe to be prior to Mar. 8, 2000).

S. Ameri et al., "Photo-Displacement Imaging", Mar. 30, 1981, pp. 337-338.

L. Chen et al., "Thermal Wave Studies of Thin Metal Films Using the Meta-Probe-A New Generation Photothermal System" 25th Review of Progress in QNDE, Snowbird, UT Jul. 19-24, 1998, pp. 1-12.

P. Alpern and S. Wurm, "Modulated Optical Reflectance Measurements on Bulk Metals and Thin Metallic Layers", J. Appl. Phys. 66(4), Aug. 15, 1989, pp. 1676-1679.

J. Opsal, "The Application of Thermal Wave Technology to Thickness and Grain Size Monitoring of Aluminum Films", SPIE vol. 1596 Metalization Performance and Reliability Issues for VLSI and ULSI (1991), pp. 120-131.

A. Rosenwaig, "Process Control In IC Manufacturing With Thermal Waves", Review of Progress in Quantitative Nondestructive Evaluation, vol. 9, 1990, pp. 2031-2037.

K. Fernaam, "Measurement of Aluminum Alloy Grain Size on Product Wafers and its Correlation to Device Reliability", 1990 WLR Final Report, pp. 97-106.

B.C. Forget et al., "High Resolution AC Temperature Field Imaging", Electronic Letters Sep. 25, 1997, vol. 33 No. 20, pp. 1688-1689.

C. Paddock et al., "Transient Thermoreflectance from Metal Films", May 1986 vol. 11, No. 5 Optical Letters, pp. 273-275.

C. Paddock et al., "Transient Thermoreflectance from Metal Films", J. Appl. Phys. 60(1), Jul. 1, 1986, pp. 285-290.

Per-Eric Nordail et al. "Photothermal Radiometry", Physica Scripts, vol. 20, 659-662, 1979.

A. Rosenwaig, "Thermal Wave Monitoring and Imaging of Electronic Materials and Devices", pp. 73-109.

W. Lee Smith et al., "Voids, Notches and Micros-cracks in Al Metallization Detected by Nondestructive Thermal Wave Imaging", Jun. 23, 1989, pp. 211-221.

W. Lee Smith et al., Imaging of Subsurface Defects in ULSI Metalization (AI Voids SI Precipitates, Silicide Instability) and SI Substrates (D Defects), Technical Proceedings Simicon/Japan 1992, Nippon Convention Center, Japan pp. 238-246.

W. Lee Smith, "Nondestructive Thermal Wave Imaging of Voids & Microcracks in Aluminum Metallization", 1989 WLR Final Report, pp. 55-68.

W. Lee Smith, "Direct Measurement of Stress-Induced Void Growth by Thermal Wave Modulated Optical Reflectance Imaging", 1991 IEEE/IRPS, pp. 200-208.

W. Lee Smith, "Evaluating Voids and Microcracks in Al Metalization", Semiconductor International, Jan. 1990, pp. 232-237.

C. G. Welles et al., "High-Resolution Thermal Wave Imaging of Surface and Subsurface Defects in IC Metal Lines", Materials Research Society, SF Marriott, Apr. 27-May 1, 1992, pp. 1187-1191.

L. Fabbri et al., "Analysis of Local Heat Transfer Properties of Tapecast AlN Ceramics Using Photothermal Reflectance Microscopy", 1996 Chapman & Hall, pp. 5429-5436.

J. A. Batista et al., "Biased MOS-FET and Polycrystalline Silicon Tracks Investigated by Photothermal Reflectance Microscopy", pp. 468-469, (believed to be prior to Mar. 8, 2000).

L. Chen et al., "Meta-Probe: A New Generation Photothermal System For Thin Metal Films Characterization"(believed to be prior to Mar. 8, 2000).

L. Chen et al., "Thermal Wave Studies of Thin Metal Films and Structures", (believed to be prior to Mar. 8, 2000).

9th International Conference on Photoacoustic and Photothermal Phenomena Conference Digest, Jun. 27-30, 1996 Nanjing, P.R. China, pp. 81.

R. S. Sharpe, Research Techniques in Nondestructive Testing vol. VII, Academic Press 1984, pp. 158-365.

R. L. Thomas et al., "Thermal Wave Imaging For Nondestructive Evaluation" 1982 Ultrasonic Symposium, pp. 586-590.

G. Slade Cargill III, "Electron-Acoustic Microscopy", Physics Today, Oct. 1981, pp. 27-32.

A. Rosencwaig, "Thermal Wave Microscopy", Solid State Technology, Mar. 1982, pp. 91-97.

Eric A. Ash, "Acoustical Imaging" vol. 12, Plenium Press, Jul. 19-22, 1982, pp. 61-65.

Entire File History of U.S. Appl. No. 09/788,273 (including Office Action Dated Feb. 12, 2004).

Entire File History of U.S. Appl. No. 10/090,316.

Entire File History of U.S. Appl. No. 09/974,571.

Entire File History of U.S. Appl. No. 10/090,287.

Entire File History of U.S. Appl. No. 10/090,262.

Entire File History of U.S. Appl. No. 09/095,805.

Entire File History of U.S. Appl. No. 10/722,724.

PCT Written Opinion for Application No. PCT/US01/07475, Feb. 27, 2002 (2 pages).

Bristow, Thomas C. and Dag Lindquist, "Surface Measurements With A Non-Contact Nomarski-Profiling Instrument", Interferometric Metrology, SPIE vol. 816, Aug. 1987, pp. 106-110.

Walter G. Driscoll and William Vaughan, "Handbook of Optics", 1978, pp. 8-42, 8-43, 8-107, and 10-72 to 10-77.

Charles Kittel, "Introduction to Solid State Physics", Fourth Edition, John Wiley & Sons, published prior to Mar. 1, 2002, pp. 262-264.

Rolf E. Hummel, "Electronic Properties of Materials, An Introduction For Engineers", published prior to Mar. 1, 2002, pp. 137-145.

H.S. Carslaw and J.C. Jaeger, "Conduction of Heat In Solids", Second Edition, published prior to Mar. 1, 2002, pp. 64-66.

"Process Monitoring System", Quantox Product Brochure, 3 pages, published prior to Mar. 1, 2002.

S. Wolf and R. N. Tauber, "Silicon Processing For The VLSI Era", vol. 1, 1986, pp. 388-399.

Yaozhi Hu and Sing Pin Tay, "Spectroscopic ellipsometry investigation of nickel silicide formation by rapid thermal process", J. Vac. Sci. Technology, American Vacuum Soc. May/Jun. 1998, pp. 1820-1824.

Dieter K. Schroder "Semiconductor Material And Device Characterization", John Wiley & Sons, Inc. 1990, pp. 538-561, and 458-466.

Quality Today News, article entitled "In-Line Metrology SEM System with 3D Imaging" dated Jan. 10, 2000 and published at http://www.qualitytoday.com/Jan-00-news/011000-3.htm before Apr. 4, 2001.

Amirtharaj et al., "Optical Properties of Semiconductors",*Handbook of Optics*, vol. II, McGraw-Hill, Inc., 1995, pp. 36.67-36.68, 36.95 and Table 11.

Eikelboom et al., "Microwave Detection of Minority Carriers in Solar Cell Silicon Wafers", *Solar Energy Materials and Solar Cells*, Elsevier Science B.V., Oct. 1995, pp. 169-185.

Grove, "Physics and Technology of Semiconductor Devices", John Wiley & Sons, Inc., 1967, pp. 326.

Jackson, "Classical Electrodynamics", John Wiley & Sons, Inc., 1962, pp. 222-226.

J. Kölzer et al., "Thermal Imaging and Measurement Techniques for Electronic Materials and Devices", *Microelectronic Engineering*, XP004006637, Elsevier Publishers BV., Amsterdam, NL, ISSN, 0167-9317, vol. 31, 1996, pp. 251-270.

C. Martinsons et al., "Recent progress in the measurement of the thermal properties of hard coatings", Thin Solid Films, XP004147705, Elsevier-Sequoia S.A. Lausanne, CH, ISSN, 0040-6090, vol. 317, Apr. 1998, pp. 455-457.

Opsal et al., "Thermal-Wave Detection and Thin-Film Thickness Measurements with Laser Beam Deflection", *Applied Optics*, vol. 22, No. 20, Oct. 1983, pp. 3169-3176.

Orton et al., "The Electrical Characterization of Semiconductors: Measurement of Minority Carrier Properties", Academic Press, 1990, pp. 94-100.

Paquin, "Properties of Metals", *Handbook of Optics*, vol. II, McGraw-Hill, Inc., 1995, pp. 35.3-35.7.

"Process Monitoring System", Quantox Product Brochure, 3 pages.

Rosencwaig, "Thermal Wave Characterization and Inspection of Semiconductor Materials and Devices", Chapter 5 (pp. 97-135) of *Photoacoustic and Thermal Wave Phenomena in Semiconductors*, North-Holland, 1987.

Rosencwaig et al., "Detection of Thermal Waves Through Optical Reflectance", *Appl. Phys. Lett. 46*, Jun. 1985, pp. 1013-1015.

Rosencwaig, "Thermal-Wave Imaging", *Science*, vol. 218, No. 4569, Oct. 1982, pp. 223-228.

Schroder, "Semiconductor Material and Device Characterization", John Wiley & Sons, Inc., 1990, pp. 2-20, 84-85, 232-235, 304-306, 364, 367-374, 378-383.

Sze, "Physics of Semiconductor Devices", John Wiley & Sons, Inc., 1981, pp. 50-51.

Entire Prosecution History of U.S. Appl. No. 09/521,232, filed Mar. 8, 2000 by Peter G. Borden et al.

Entire Prosecution History of U.S. Appl. No. 09/095,804, filed Jun. 10, 1998 by Peter G. Borden et al.

Entire Prosecution History of U.S. Appl. No. 09/274,821, filed Mar. 22, 1999 by Peter G. Borden et al.

International Search Report, PCT/US01/07475 dated Oct. 23, 2001, pp. 5.

* cited by examiner

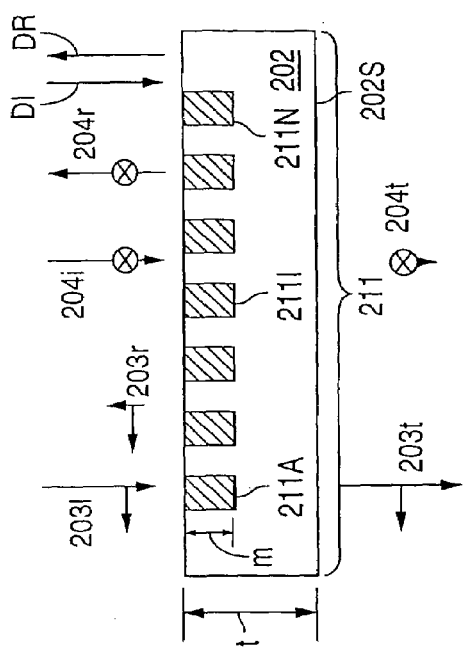
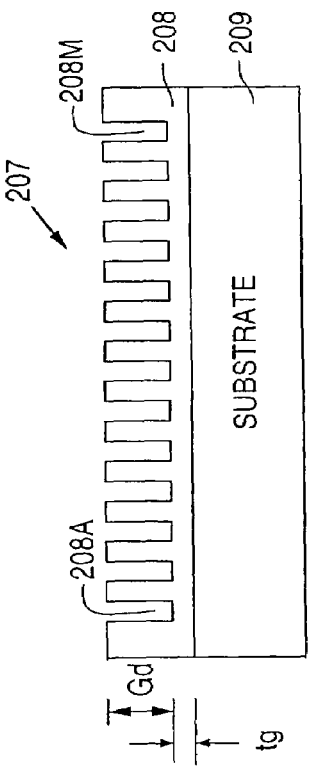
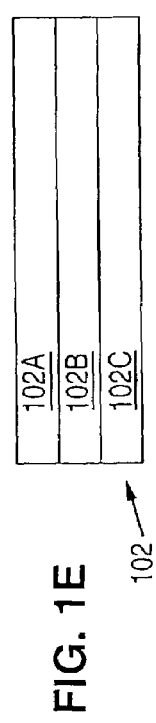
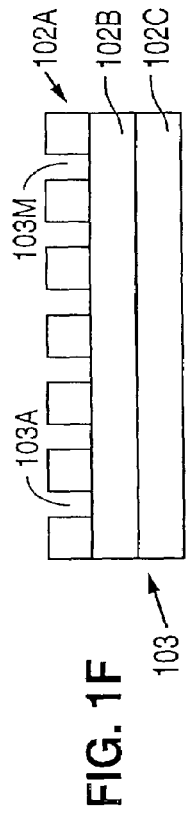
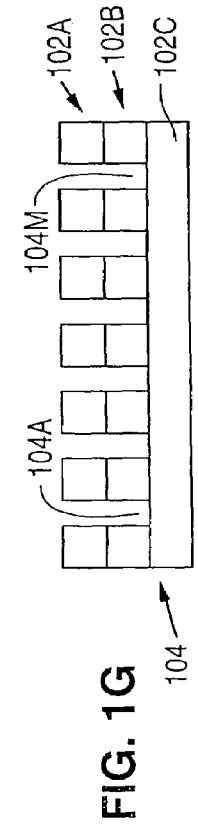
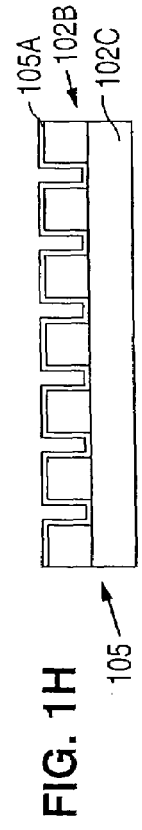
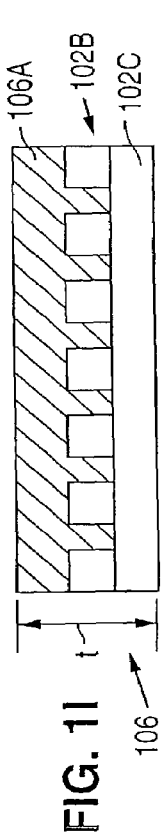
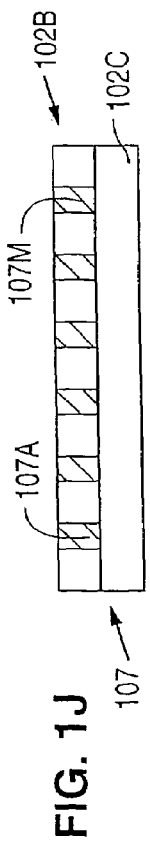
FIG. 2A
FIG. 2B
FIG. 1E
FIG. 1F
FIG. 1G
FIG. 1H
FIG. 1I
FIG. 1J

FIG. 3E
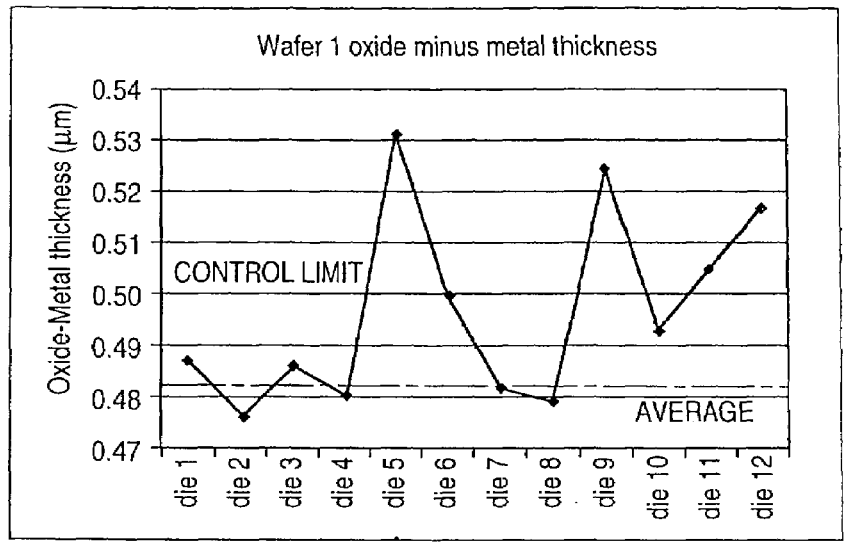
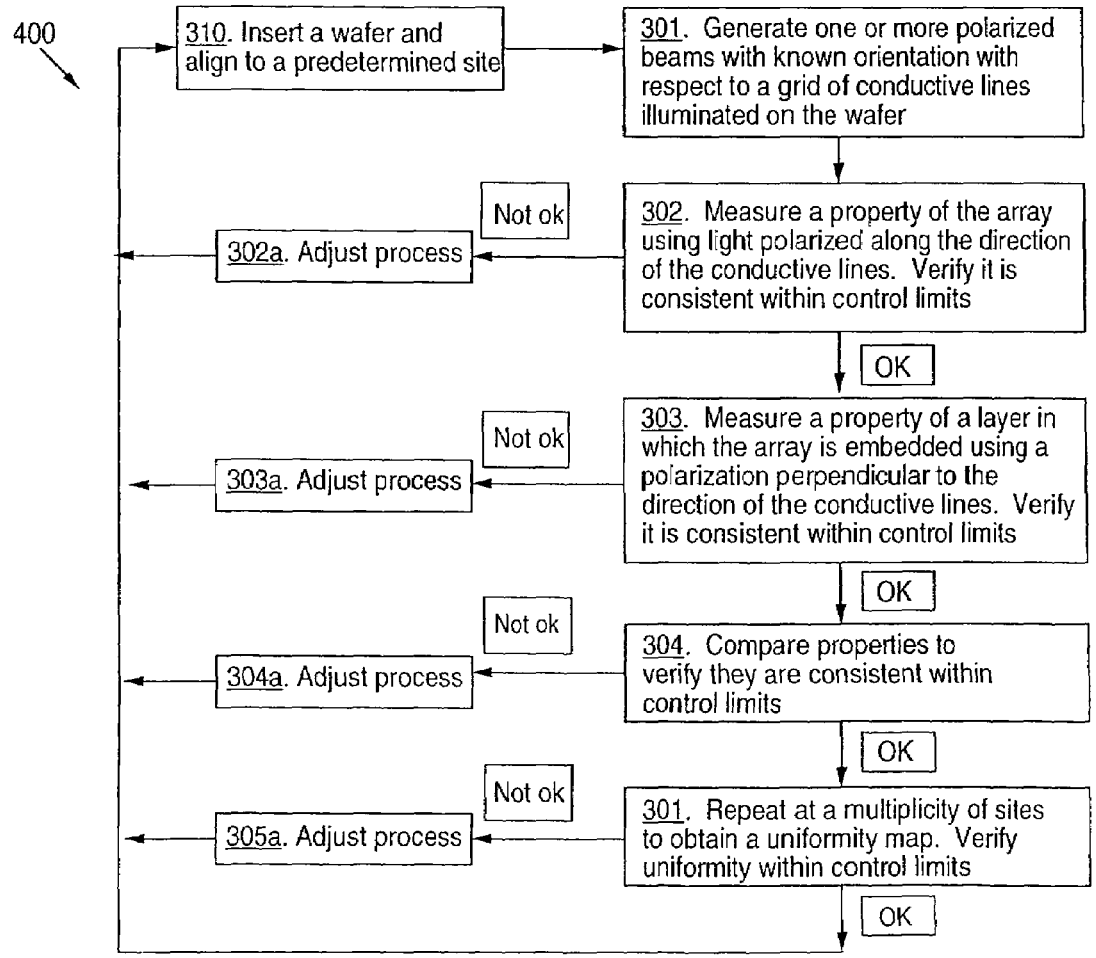
FIG. 4A

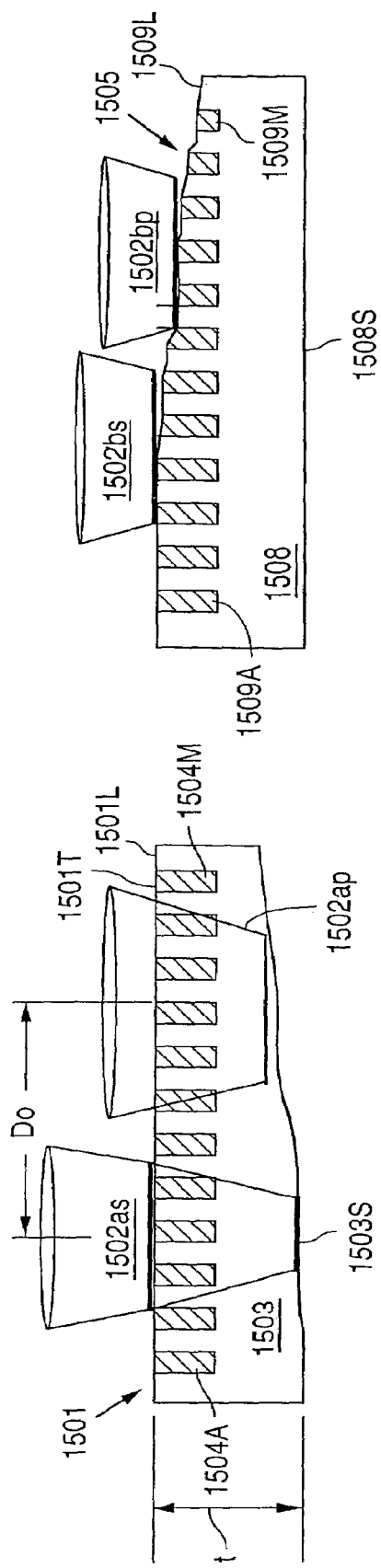
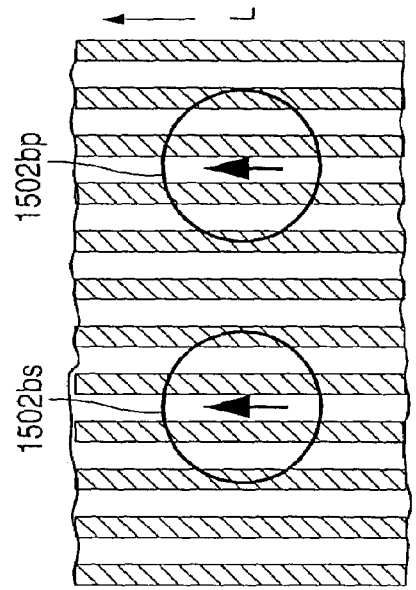
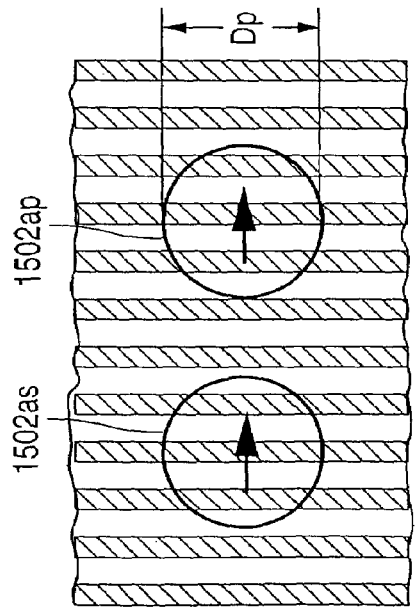
FIG. 7A
FIG. 7B
FIG. 7C
FIG. 7D

EVALUATING A GEOMETRIC OR MATERIAL PROPERTY OF A MULTILAYERED STRUCTURE

CROSS-REFERENCE TO PRIORITY APPLICATION

This application is a continuation of U.S. patent application Ser. No. 09/521,232 filed Mar. 8, 2000, which is incorporated by reference herein in its entirety.

CROSS-REFERENCES TO RELATED APPLICATIONS

This application is related to and incorporates by reference herein in their entirety, the following commonly owned, copending U.S. patent applications:

Ser. No., 09/095,805, entitled "AN APPARATUS AND METHOD FOR MEASURING A PROPERTY OF A LAYER IN A MULTILAYERED STRUCTURE," filed Jun. 10, 1998, by Peter G. Borden et al;

Ser. No. 09/095,804, entitled "APPARATUS AND METHOD FOR EVALUATING A WAFER OF SEMICONDUCTOR MATERIAL," filed Jun. 10, 1998, by Peter G. Borden et al; and Ser. No. 09/274,821, entitled "APPARATUS AND METHOD FOR DETERMINING THE ACTIVE DOPANT PROFILE IN A SEMICONDUCTOR WAFER," filed Mar. 22, 1999, by Peter G. Borden et al.

BACKGROUND

In the processing of a semiconductor wafer to form integrated circuits, a number of traces are normally formed over an underlying layer. The traces are normally used to interconnect transistors and other devices in the integrated circuits. Such traces may have widths under 0.2 micrometers (microns), pitches (center to center spacing) under 0.4 microns and aspect ratios exceeding 4:1.

Depending on the stage of the processing, it may be necessary to measure properties of various portions of a wafer, such as the properties of the traces and/or the properties of the underlying layer. However, the presence of traces can interfere with conventional measurements that examine open areas (areas not covered by traces).

SUMMARY

A structure having a number of lines supported by a layer in contact with the lines (also called "multi-layered structure") is evaluated in accordance with the invention by illuminating a region (also called "illuminated region") containing several lines, using a beam of electromagnetic radiation, and generating an electrical signal (e.g., by use of a photosensitive element) that indicates an attribute (e.g., intensity or optical phase) of a portion (also called "reflected portion") of the beam reflected from the region. As more than one line (and therefore more than one portion of the layer in contact with the lines) is being illuminated, the reflected portion and the electrical signal generated therefrom do not resolve individual features in the illuminated region, and instead indicate an average measure of a property of such features. In contrast, most prior art methods measure a property of an individual feature in such a multi-layered structure. The just-described lines can be either conductive (in which case they are also referred to as "traces" or non-conductive, depending on the embodiment.

In one embodiment, the acts of "illuminating" and "generating" are repeated in another region (of the same structure or of a different structure) also having multiple traces. The electrical signals being generated from light reflected by different regions can be automatically compared to one another to identify variation of an average property (e.g., average thickness of the layer in contact with the traces, or average resistance per unit length of the traces) between the regions. Instead of (or in addition to) the just-described comparison, the values of such a signal can be plotted in a graph to indicate a profile of a surface in the region. A value being plotted can be an absolute value of the reflected portion alone, or can be a value relative to another portion that is reflected by another surface in the same region (which indicates the average distance therebetween), or by the same surface in another region (which indicates an average profile of the surface).

Such measurements can identify variations in properties in a semiconductor wafer of the type used in fabrication of integrated circuit dice, or between multiple such wafers (e.g., values measured from a reference wafer and a production wafer or between two successive production wafers can be compared). Identification of a change in a property between two or more wafers is useful e.g., when performing such measurements during wafer fabrication, so that process parameters used to fabricate a next wafer (e.g., creating the above-described layer or the traces) can be changed as necessary (in a feedback loop), to generate wafers having material properties within acceptable limits. Note, however, that structures other than semiconductor wafers (e.g., photomasks that include a glass substrate and are used to form the wafers, or an active matrix liquid crystal display) can also be evaluated as described herein.

In a first example, there is a transmissive medium (such as air) located between a source of the beam (also called probe beam) and the illuminated region. In one implementation, another beam (also called "heating beam") is used in addition to the probe beam, to modulate the temperature of the traces (e.g., at a predetermined frequency). Reflectance of the lines changes with the change in temperature. The reflected portion (which depends on reflectance), and hence the generated signal also oscillates (e.g., as the predetermined frequency). Such an oscillating signal is measured by e.g., a lock-in amplifier, and the measurement is repeated in another region. If all lines in the illuminated region are conductive (also referred to as "traces"), comparison of measurements from different regions (e.g., which may be in the same location in different die of a wafer, or which may be in the same die in different wafers) indicates a change in the average resistance per unit length (and therefore the corresponding change in cross-sectional area) between traces in the respective regions (if conductivity is constant).

A series of measurements from regions adjacent to one another (or even overlapping one another) in the longitudinal direction of the traces, when plotted in a graph along the y axis with the x axis indicating distance along the longitudinal direction yields a profile of the traces (which may be used to detect, e.g. global nonuniformity such as a dimple or a dome). Depending on the specific variant, the probe beam and the heating beam can each be coincident with or offset from the other.

In another implementation, multiple traces in a region of a structure of the first example are each substantially parallel to and adjacent to the other, and the beam has wavelength greater than (or equal) to a pitch between two adjacent traces. In one such embodiment, the probe beam is polarized (e.g., by a polarizing optical element interposed between a source of the beam and the structure), although a nonpolarized probe beam can be used in other embodiments. A polarized probe beam can be used in several ways, including, e.g., orienting the probe beam so that the electrical field vector for the electromagnetic radiation is at a predetermined angle relative to the traces.

When the probe beam is polarized perpendicular to the traces, the traces do not reflect the probe beam. Instead, the probe beam passes between the traces and is reflected from underneath the traces, e.g. by charge carriers of a semiconductor layer, or by a surface of an oxide layer, or both. Such light which is reflected from underneath the traces can be used to identify variation in a property of features underneath the traces (averaged over the features that are illuminated). The portion reflected by charge carriers is relatively small (e.g., $\frac{1}{10}$ or less) as compared to the portion reflected by an underlying surface, and therefore has a negligible effect on an overall measurement of a steady signal (also called "DC" component). If necessary, the portion reflected by charge carriers can be measured by modulating the number of charge carriers and using a lock-in amplifier to measure the portion of a reflected light that is modulated (also called "AC" component) as described elsewhere herein. The charge carriers can be created by a beam having an oscillating intensity (or oscillating phase). In this variant, the reflected portion has an intensity (or phase) that is modulated in phase with modulation of the charge carriers (and can be measured by use of a lock-in amplifier).

When the probe beam is polarized parallel to the longitudinal direction of the traces, the above-described reflected portion (that is used to generate the electrical signal) is reflected by the traces. The reflected portion can be used to identify variation in a property that is averaged over the traces. A probe beam polarized parallel to the traces can be used with a heating beam that is also polarized parallel to the traces, and in such a case effectively on the traces interact with the heating beam, and are heated more, as compared to heating by an unpolarized heating beam. Alternatively, the just-described probe beam (also called "parallel polarized beam") can be used with another probe beam that is polarized perpendicular to the traces (also called "perpendicular polarized beam"). The two polarized beams can be generated from the same beam, e.g., by a polarizer or a polarizing optical element (such as a Wollaston beam splitter), or by a combination of such optical elements (e.g. Wollaston beam splitter followed by a polarizer). A polarizer here refers to any optical element or set of optical elements whose output is a beam with a single direction of polarization.

In one embodiment, a portion of the parallel polarized beam reflected by the traces, and a portion of the perpendicular polarized beam reflected from underneath the traces interfere, and the interference pattern is used to generate an electrical signal. As noted above, the electrical signal indicates a profile of the underneath surface when the beams are offset. When the parallel polarized beam and the perpendicular polarized beam are coincident, the electrical signal indicates a distance between the underneath surface and a surface of the traces exposed to the transmissive medium (also called "exposed surface"). Note that the exposed surface of the structure can be formed by a surface of the traces and a surface of the layer that interdigitates between the traces (the layer surface and the trace surface can be substantially co-planar—within the same plane or in planes that are separated from each other by less than 10% of the width of the traces) and such surfaces can be formed, e.g., by chemical mechanical polishing.

The two probe beams that are polarized mutually perpendicular to each other can each be oriented at 45° relative to the traces, so that at least a portion of each beam is reflected from the exposed surface of the structure. In such a case, the electrical signal obtained from the two or more reflected portions indicates a profile of the exposed surface, assuming the two beams are offset from one another, and the surface containing the traces has a constant profile. An optional polarizing beam splitter can be used to limit the measurement to the two portions that are reflected by the traces (or to the two portions that are reflected by a surface underneath the traces when profiling the underneath surface). Therefore, illuminating a region containing two or more traces allows use of the wafer as a polarizer to measure an average property of features underneath the traces that are otherwise inaccessible.

In a second example, the traces are separated from the transmissive medium by a layer (also called "exposed layer") included in the structure. One method used with the second example measures a signal obtained from interference between a portion of the probe beam reflected by the traces, and another portion reflected by a layer formed over the traces. Reflection of a perpendicular polarized beam by the exposed layer overcomes a prior art problem of illuminating a region containing traces, because the traces do not adversely affect the perpendicularly polarized light (e.g., the traces reflect parallel polarized light). The just-described method does not require a heating beam. This method also has the advantage of being able to measure a property of traces buried underneath the exposed layer.

In a variant of the just-described method, both portions are reflected by the traces, and each portion is offset from the other thereby to yield a signal indicative of a profile of the surface of traces (although the traces are located underneath the exposed layer). In such a method, the to-be-reflected portions of a probe beam can be polarized mutually perpendicular to each other and oriented at 45° relative to the traces. Instead of mutually perpendicularly polarized beams, two beams that are polarized parallel to one another and also parallel to the traces also can be used, e.g., to obtain a surface profile of the traces (that are located underneath the exposed layer).

Furthermore, instead of being offset from one another, the parallel polarized beams can be coincident, with one beam being the probe beam and the other beam being the heating beam. In such a case, the measured signal provides an indication of a property of the traces, although the traces are located underneath the exposed layer. If the two beams that are polarized parallel to one another (e.g., a probe beam and a heating beam) are both oriented perpendicular to the traces (a first set) underneath the exposed layer, a property of a second set of traces located underneath the first set can be determined. Furthermore, instead of a heating beam, a pump beam can be used to generate charge carriers in a layer located underneath the traces.

One implementation combines two of the above-described methods, by using two beams that are respectively polarized parallel and perpendicular relative to the longitudinal direction of a set of traces in the structure. In this implementation, two electrical signals for two measurements in the two polarization directions are generated contemporaneously (e.g., just before, during or just after each other). Simultaneous generation of the two electrical signals provides an advantage in speed, as compared to sequential generation of the two signals. Such electrical signals can provide measures of properties of both traces and a layer underneath the traces, so that a wafer can be accepted or rejected in a signal operation.

In another embodiment, the probe beam is nonpolarized (or has circular or elliptical polarization so that both orthogonal polarization components are simultaneously present in the single probe beam). In one implementation of this embodiment, the method includes generating a single electrical signal from the portion of light reflected when a nonpolarized (or circular or elliptical polarized) probe beam is used. In another implementation, the method includes contemporaneous generation of two electrical signals based on measurement of two components of the reflected portion: a first component that is polarized in a direction perpendicular to the traces, and a second component that is polarized in a direction parallel to the traces.

BRIEF DESCRIPTION OF THE DRAWINGS

FIGS. 1E-1J illustrate, in partial cross-sectional views, a semiconductor wafer at various stages of fabrication in the apparatus of FIG. 1D.

FIG. 2A illustrates, in a partial cross-sectional view, the relationship between two polarized components of a probe beam and the light reflected by or passing between the traces in a semiconductor wafer.

FIG. 2B illustrates, in a cross-sectional view, a structure having grooves 208A-208M that contain a gas, such as air that acts as a number of non-conductive traces, and which can also be used as a polarizer as described herein.

FIGS. 3C-3E illustrate, in graphs, relationships between measurements of the two polarized components in one example.

FIG. 4A illustrates, in a flow chart, acts performed during wafer fabrication in one implementation of the embodiment illustrated in FIG. 1C.

FIGS. 7A-7E are similar or identical to the corresponding FIGS. 6A-6E except that the polarization directions of the two beams are parallel to one another.

DETAILED DESCRIPTION

Figure 1A:
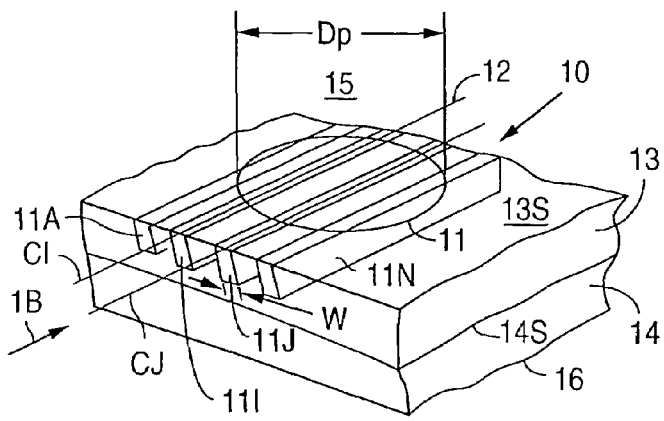
FIG. 1A illustrates, in a perspective view, a portion of a structure having a number of traces in a region illuminated by a probe beam in accordance with the invention.

A structure 10 (FIG. 1A) is multilayered, and contains a number of lines 11A-11N (A $\leq$ I $\leq$ J $\leq$ N; N being the total number of lines) passing through a region 11 (also called illuminated region) of a layer 13. Lines 11A-11N have an index of refraction different from the index of refraction of layer 13, and therefore reflect a probe beam that is directed at region 11. Note that lines 11A-11N need not be conductive, although. in one embodiment the lines are conductive. For this reason, in the following description, the term "lines" is used generically, and when referring specifically to embodiments involving lines that are formed of conductive material, the term "traces" is used. Embodiments involving other kinds of lines are apparent to the skilled artisan in view of the disclosure (e.g. see the description below in reference to FIGS. 2B and 2F). Structure 10 can be (but is not required to be) a wafer of the type commonly used to manufacture integrated circuit dies. Note also that lines 11A-11N need not be parallel to each other (except when a polarized probe beam is used as discussed below in which case lines 11A-11N are at least substantially parallel to each other).

Structure 10 is evaluated in one embodiment of the invention by focusing (see act 22 in FIG. 1C) a beam 12 (FIG. 1A) of electromagnetic radiation on region 11 (which is defined to be the entire region illuminated by beam 12 on an exposed surface 13S of structure 10). Beam 12 has a diameter d (at surface 13S of structure 10) that is selected to be several times larger than the width w of a line 11I For example, diameter d can be 2 microns and width w can be 0.15 microns (so that seven lines are simultaneously covered by beam 12).

Note that beam 12 merely illuminates region 11 and may or may not be focused on surface 13S (which is a surface of structure 10 exposed to a transmissive medium 15 such as air). In different embodiments, beam 12 is focused on (a) surface 13S, (b) surface 14S, (c) between surfaces 13S and 14S, (d) surface 16, or (3) above surface 13S. Therefore, beam 12 does not resolve individual features in region 11 (unlike a scanning microscope of the prior art which can resolve the individual features). Instead, beam 12 is used to obtain an average measure of one or more properties in illuminated in region 11, e.g., of lines 11A-11N, or of layer 13 or a combination thereof, or some other material or feature in region 11. layer 13 or a combination thereof, or some other material or feature in region 11.

A portion of beam 12 is reflected by region 11, and is used to generate (e.g., as illustrated by act 23 in FIG. 1C) an electrical signal (e.g., by use of a photosensitive element) that indicates an attribute (e.g., intensity or optical phase) of the reflected portion. The measured attribute in turn is used as an average measure of a property of a material in region 11. For example, if the just-described acts 22 and 23 are performed in one region 11, a stage that supports structure 10 moves structure 10 so that a different region is illuminated, and then these acts 22 and 23 are repeated. Therefore, this embodiment involves stepwise movement ("hopping") from one region to another region of structure 10 when performing measurements of the type described herein (as opposed to a scanning microscope of the prior art that continuously moves ("sweeps") a beam of electromagnetic radiation relative to a structure). In the hopping process, the stage holds structure 10 stationary for a moment (e.g., 1 second) while a measurement is taken in one region, and then moves to another region (e.g., of the same structure).

Two regions in which measurements are made can be separated from each other, e.g., by distance which is same as the diameter Dp of beam 12. Alternatively, the two regions can touch each other or even overlap each other. When overlapping one another, the centers of the two regions may be separated by a small fraction of the diameter, e.g., by ($1/10$) Dp or less. Regardless of how close the regions are, the hopping process yields discrete values (one for each region) as compared to the sweeping process which yields a continuous signal. As described elsewhere herein, the regions can be physically located in different structures, so that an alternative embodiment involves hopping from structure to structure (when hopping among regions). A combination of the just-described two types of hopping can also be used (i.e., moving between regions of the same structure and also moving between regions of different structures).

Note that the just-described "hopping" can be performed from one region to a next region that touch each other, and a measurement from each region can be plotted in a graph, e.g., to indicate a profile of a surface across the regions. As described elsewhere herein, such measurements provide an average profile (in view of nonresolution of the individual features in the illuminated region). In another embodiment, the hopping is performed between regions that overlap one another thereby to provide a more realistic measure of the average profile across these regions, as compared to non-overlapping regions.

The electrical signals obtained by the measurements are optionally compared (e.g., in act 24) either against each other or against a predetermined limit, to identify a change in a property (such as the thickness of layer 13 or thickness lines 11A-11N) between the regions. An electrical signal indicative of reflectance changes in response to a change in a property of features (such as layer 13 or lines 11A-11N) containing the material being evaluated in structure 10. Note that the electrical signal by itself provides an average measure of the property in the region due to the region having a size that is larger (e.g., by an order of magnitude) than to size of an individual feature.

Note also that only changes that cause a property to fall outside a predetermined range are flagged in one embodiment. Such a predetermined range can be same as the limits beyond which a structure is rejected as being unacceptable (or can be smaller than such limits to allow a correction to be made even before an unacceptable structure is fabricated). Note that the property being measured can be an average dimension of the features in region 11 (such as thickness of traces) or an average material property of such features (such as the average resistance per unit length of the traces).

Comparisons of such signals from different regions (of a structure or structures) may be performed manually, although in other examples such comparisons are performed automatically (by a programmed computer). Alternatively, the electrical signals generated in act 23 can be plotted to obtain a two dimensional image of structure 10 as a whole, so that the image indicates changes in property (also called "material property") between such regions. Instead of a two-dimensional image, the electrical signals can be plotted in a graph along the y axis, with the x axis representing regions in structure 10.

As noted above, the just-described regions can be inside a single structure 10, or spread across multiple such structures (e.g., in a reference structure that has known material properties, and a production structure that is currently being fabricated and whose properties are yet to be determined, or even multiple production structures). Identification of changes in a property between two or more structures is useful e.g., when performance of such measurements is interleaved between fabrication processes, so that one or more process parameters used to fabricate a next structure (such as creating traces or a layer adjacent to the traces, as illustrated by optional act 21) can be changed as necessary (e.g., as illustrated by optional act 25) to fabricate structures having properties within acceptable limits.

Note that acts 21, 24 and 25 described above in reference to FIG. 1C are optional, and may or may not be performed, depending on the embodiment. For example, the generated electrical signals may be manually evaluated. Alternatively, such evaluations (manual or automatic) may be performed independent of the fabrication processes of the structures. In one embodiment, the above-described structure 10 is implemented as a semiconductor substrate (also called "wafer") of the type used in fabrication of integrated circuit dice. In this embodiment, a processing unit 100 (FIG. 1D) creates integrated circuit (abbreviated as "IC") dice by processing a semiconductor substrate 102 (FIGS. 1D and 1E) to form various substrates 103-107 (FIGS. 1F-1J) at intermediate stages in the fabrication of the dies.

In one example, a patterning apparatus 120 deposits a photoresist layer 102A on top of an insulation layer 102B which in turn is formed on silicon substrate 102C (FIG. 1E). In this example, an etching apparatus 121 exposes and develops photoresist layer 102A to form therein grooves 103A-103M (M being the total number of grooves), thereby to form wafer 103 (FIG. 1F). Thereafter, an etching apparatus 121 etches through the patterned photoresist layer 102A to form grooves 104A-104M in insulation layer 102B, thereby to form wafer 104 (FIG. 1G).

Next, resist layer 102A is removed, and a liner deposition apparatus 122 forms a barrier layer 105A (e.g., of tantalum nitride to prevent diffusion of to-be-applied conductive material, such as copper, into insulation layer 102B) in etched grooves 104A-104M of insulation layer 102B, as illustrated by wafer 105 in FIG. 1H. Then a conductive material 106A is blanket deposited on wafer 105, by a deposition apparatus 123 thereby to form substrate 106 (FIG. 1I). Note that barrier layer 105A, although present in substrate 106, is not shown for clarity in FIG. 1I. The deposited layer 106A has a thickness t (FIG. 1I) of, for example, 1-2μm. Next a polishing apparatus 124 is used to polish back layer 106A (e.g., by 1-2μm), leaving conductive lines 107A-107M (also called "traces") in grooves of insulation layer 102B, as in the case of a damascene structure.

Processing unit 100 includes a measuring apparatus 125 (FIG. 1D) that performs the process described above in reference to FIGS. 1A-1C. Therefore, at any point during wafer fabrication of the type described above in reference to FIGS. 1D-1J, a wafer can be subjected to the measurement process e.g., as illustrated by arrows 110-114. If a measured signal falls outside a predetermined limit (e.g., exceeds a maximum or falls below a minimum), the fabrication process can be adjusted in real time, thereby to produce more wafers that are acceptable (than if measurements were done after wafers are fabricated). The predetermined limit can be selected after calibration, e.g. from a signal obtained when the measurement process is performed on a wafer having known properties (which are properties determined by use of any prior art method).

One embodiment of apparatus 125 includes an optional programmed computer 126 that supplies a process parameter (used in the fabrication process) on a bus 115 that is coupled to each of apparatuses 120-124 described above. A change in the process parameter can be determined automatically by software in programmed computer 126 (e.g. by performing a table look up), or can be entered by a human operator. Note that in one embodiment a single measurement operation on wafer 107 measures properties of traces 11A-11N (FIG. 1A) and also of layer 13, so that multiple measurement operations are not required.

In one embodiment, traces 11A-11N (FIG. 1A) are each substantially parallel to and adjacent to the other (e.g., centerlines CI and CJ of traces 11I and 11J that are adjacent to each other form an angle of less than 25° relative to one another). In this embodiment, beam 12 is selected to have a wavelength greater than or equal to pitch p between two adjacent traces 11I and 11J. In one implementation of such an embodiment, measurement apparatus 125 (FIG. 1D) determines, between two or more acts of fabricating substrate 102, an average measure of the thickness t of layer 13 in region 11 (FIG. 1A), simply by measuring the intensity of the portion of beam 12 reflected from region 11.

Note that another beam (also called "pump beam"), in addition to beam 12, can be used to create charge carriers in layer 14 (e.g., as described in the related patent application, U.S. patent application Ser. No. 09/095,804) if layer 14 is formed of a semiconductor material. In one such example, beam 12 (also called "probe beam") contains photons having energy lower than or approximately (within 10%) equal to the bandgap energy of a semiconductor material in layer 14. In the example, charge carriers may be modulated in any one or more of several ways: (1) by photogeneration of additional charge carriers; (2) movement of background carriers due to change in voltage potential caused by illumination or some other way.

In one embodiment the charge carriers are modulated at a frequency that is sufficiently low to avoid creation of a wave of charge carriers. If so modulated, the reflected portion of beam 12 is also modulated at the just-described frequency, in phase with modulation of the charge carriers (and the reflected portion of beam 12 can be measured by use of a lock-in amplifier as stated in the just-described patent application).

Beam 12 can be linearly polarized, circularly polarized, elliptically polarized, nonpolarized or some combination thereof, depending on the implementation. So, in one implementation, probe beam 12 is nonpolarized, and one embodiment generates a single electrical signal from the reflected portion. Such an electrical signal (as a whole) provides an average measure of the thickness t of a layer 13 (FIG. 1B) that supports traces 11A-11N. In one embodiment, in addition to the nonpolarized probe beam 12, an additional beam such as the heating beam described in the related patent application Ser. No. 09/095,805 is used (as described below) to illuminate multiple traces.

In this embodiment, a modulated component of the electrical signal (as measured by a lock-in amplifier) provides a measure of a property (such as thickness) of traces 11A-11N. The modulated component of the electrical signal, obtained from measuring the change in reflectance of traces 11A-11N, is sufficiently small relative to the overall electrical signal (due to reflectance of nonpolarized probe beam 12 by region 11) so that the overall electrical signal can be used as a measure of a property of layer 13.

Therefore, a measure of the modulated component and of the overall electrical signal (or its steady component) identify a change in properties of different layers of a structure, and such measurements can be performed in a single operation. Instead of using a heating beam, if a pump beam of the type described in the related patent application Ser. No. 09/095,804 is used, then a change in a property of a semiconductor layer 14 (FIG. 1A) can be identified by use of a lock-in amplifier to measure the modulated component.

Instead of nonpolarized beam, a circularly or elliptically polarized beam can also be used as described herein for a nonpolarized beam (except that separate calibration is required for an elliptically polarized beam; specifically, in the case of elliptically polarized light, the intensities in the two directions are different: for example, if the ratio of intensity in the two directions is 2:1 (parallel:perpendicular), then the parallel signal will be twice as strong for the same reflectivity, and reflection in the parallel direction must be divided by 2 to compare to the reflection in the perpendicular direction).

In one embodiment, a reflected portion of a nonpolarized probe beam 12 is passed through a polarizer or a polarizing beam splitter to generate one or both components that have orthogonal polarization directions. For example, a polarizer may be used to select an individual polarization direction that may be oriented parallel (or perpendicular depending on the orientation of the polarizer) to a set of traces, and so that the photocell detects only parallel polarized light (and the perpendicular polarized light is blocked). Alternately, a polarizing beam splitter separates the unpolarized light into two orthogonal polarization components, for instance, aligned parallel and perpendicular to a set of traces. The parallel and perpendicular polarized components are then intercepted by separate photodetectors to simultaneously measure their individual intensities.

In the above-described embodiment, probe beam 12 can be either polarized or nonpolarized. In one implementation, probe beam 12 is linearly polarized even prior to being incident on structure 10 (e.g., by a polarizing element interposed between a source of beam 12 and structure 10). The polarizing element can be a polarizing beam splitter available from Melles Griot of Irvine Calif. (see, for example part number 033 PBB 012). A polarized probe beam 12 can be used in several ways, including, e.g., orienting beam 12 (FIG. 1K) so that the electric field vector v thereof is at a predetermined angle θ (such as 0°, 90° or 45°) relative to the longitudinal direction 1B (FIG. 1A) of traces 11A-11N.

In one example, a probe beam 203$i$ (FIG. 2A) is polarized perpendicular (i.e., θ=90°) to traces 211A-211N, which appear transparent to beam 203$i$ due to the orientation, as long as the wavelength exceeds the pitch. Therefore, probe-beam 203$i$ has energy in the form of beam 203$t$ that passes through layer 202 (that is at least partially transmissive), and the remaining energy of probe beam 203$i$ is reflected (e.g., by surface 202$s$) in the form of reflected portion 203$r$ or absorbed. The transmitted portion 203t passes between traces 211A-211N in the direction of incidence DI, because traces 211A-211N act as a polarizer, as described in, e.g., the Optics Handbook, pages 10-72 to 10-77. As described therein, the transmittances $T_1$ and $T_2$ for the grid of traces 211A-211N are:

$$(T_1)_\perp = \frac{4nA^2}{1+(1+n)^2 A^2} \quad (1)$$

$$(T_1)_\| = \frac{4nB^2}{1+(1+n)^2 B^2} \quad (2)$$

where n=refractive index of (transparent) substrate material
$(T_1)_\perp$=transmittance for radiation polarized perpendicular to the traces.
$(T_2)_\|$=transmittance for radiation polarized parallel to the traces.

The general expressions for A and B are:

$$\frac{1}{A} = \frac{4d}{\lambda}\left\{\ln\left[\csc\frac{\pi(d-a)}{2d}\right] + \frac{Q_2\cos^4[\pi(d-a)/2d]}{1+Q_2\sin^4[\pi(d-a)/2d]} + \right. \quad (3)$$

$$\left. \frac{1}{16}\left(\frac{d}{\lambda}\right)^2\left[1-3\sin^2\frac{\pi(d-a)}{2d}\right]^2\cos^4\frac{\pi(d-a)}{2d}\right\}$$

$$B = \frac{4d}{\lambda}\left[\ln\left(\csc\frac{\pi a}{2d}\right) + \frac{Q_2\cos^4(\pi a/2d)}{1+Q_2\sin c^4(\pi a/2d)} + \right. \quad (4)$$

$$\left. \frac{1}{16}\left(\frac{d}{\lambda}\right)^2\left[1-3\sin^2\frac{\pi a}{2d}\right]^2\cos^4\frac{\pi a}{2d}\right]$$

$$\text{where } Q = \frac{1}{[1-(d/\lambda)^2]^{\frac{1}{2}}} - 1 \quad (5)$$

These relations hold for traces 211A-211N having trace width a and spacing d, assuming λ>2d. Eqs. (3) and (4) are in error by less than 1 percent when λ>2d; for the condition λ>d, the error is less than 5 percent but increases for still shorter wavelengths.

When the trace width a is equal to the width of the spaces between the traces (d−2a), Eqs. (3) and (4) are simplified since 3−a=a−d/2:

$$B = \frac{d}{\lambda}\left[0.3466 + \frac{0.25Q_2}{1+0.25Q_2} + 0.003906\left(\frac{d}{\lambda}\right)^2\right] \quad (6)$$

$$A = 1/4B \quad (7)$$

Note that although traces 211A-211N are described for one embodiment, an alternative embodiment is for lines that are not conductive.

Another structure 207 (FIG. 2B) has grooves 208A-208M that hold air or other gas. Grooves 208A-208M are formed in an insulative layer 208 (that is supported on a substrate 209) by etching, e.g. as described above in reference to FIG. 1F. When a probe beam 203i is incident on structure 207, grooves 208A-208M act in a manner similar to that described herein (above and below) in reference to traces 211A-211N, except for any discussion related to a heating beam.

Specifically, there is a difference in the index of refraction between the air in grooves 208A-208M and in layer 208, and the optical effect is similar to the effect when there are traces in the grooves. Specifically, probe beam portion 203t reflected from structure 207 has an intensity that is dependent on the average depth Gd (FIG. 2F) of grooves 208A-208M (FIG. 2B). In the example illustrated in FIG. 2F, curves 301 and 303 are formed by measurements from illuminating the traces with a perpendicularly polarized beam in a structure having a 1.0 μm thick insulative layer, and having a trace width of 0.18 μm. Curve 301 is obtained when the electric field (also referred to as "TE") is oriented along grooves 208A-208M, whereas curve 302 is obtained with the electric field oriented perpendicular to grooves 208A-208M (i.e. magnetic field is oriented along the grooves). Curves 302 and 304 are formed by similar measurements from use of a parallel polarized beam, when the trace width is 0.13 μm.

Figure 3A:
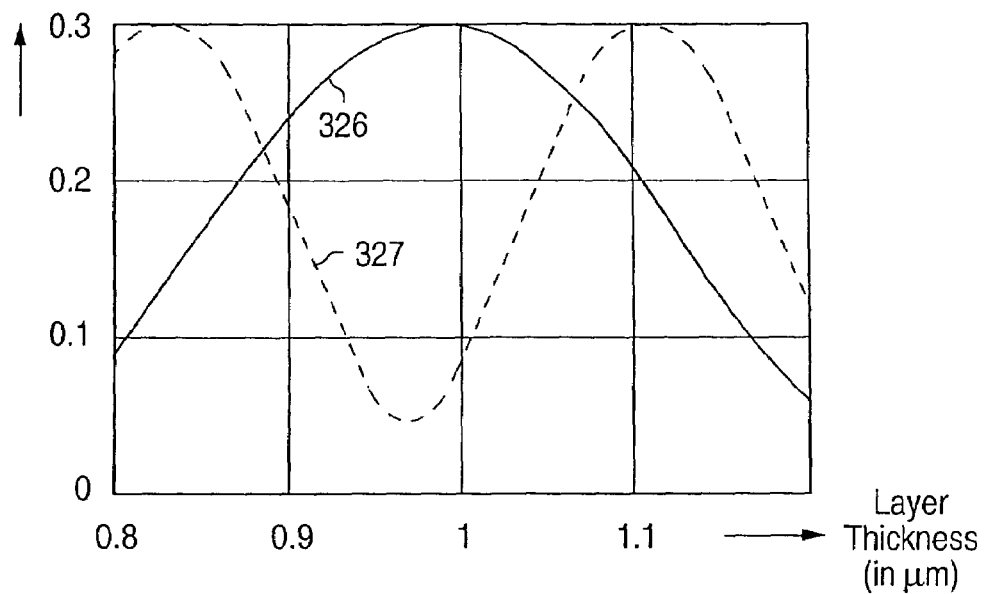
FIGS. 3A and 3B illustrate, in graphs, a change in reflectance of the region illuminated by the probe beam (illustrated in FIG. 1A) as a function of thickness of an insulative layer located underneath the traces (plotted along the x axis in μm) for FIG. 3A or thickness of traces for FIG. 3B.

The intensity of reflected portion 302r is also a function of polarization direction and of the thickness tg between the bottom surface of grooves 208A-208M and substrate 209. Performing a reflectance measurement with one probe beam and then repeating the measurement with a probe beam of a different wavelength, yields two measurements that are used with charts to extract the depth Gd and thickness tg, e.g., as described below in reference to FIG. 3A (i.e., to resolve an ambiguity). Alternatively, such reflectance measurements can be made by use of either one of two probe beams that have mutually perpendicular polarizations. Of course, both can be used successively (i.e., one after another) to obtain two reflectance measurements that can be used (with charts) to look up each of depth Gd and thickness tg. Note that grooves 208A-208M in layer 208 do not act as a sheet of metal or conductor when illuminated by a beam polarized parallel to the longitudinal direction of the grooves.

For a given wavelength λ of probe beam 12, as the pitch p is reduced below λ (and the number of traces in region 11 is increased correspondingly) a parallel polarized beam is reflected more effectively and a perpendicular polarized beam is transmitted more effectively. Specifically, an extinction ratio increases with reduction of pitch, as illustrated by curves 221-223 in FIG. 2C which illustrate the extinction ratio for light at a wavelength of 0.98 μm as a function of the pitch in microns. The extinction ratio is the ratio determined by dividing the transmission for light polarized perpendicular to the lines by the transmission for light polarized parallel to the traces. Curve 222 is for trace width equal to half the pitch. Curve 221 (solid line) is for the case of traces being 10 % wider than the half-pitch (trace width equals pitch/1.8 μm). Curve 223 (dashed line) is for the case of traces 10 % narrower than the half-pitch (trace width equals pitch/1.2 μm).

Therefore when pitch is approximately equal to the wavelength, both polarized components are transmitted equally. So, in one embodiment, wavelength greater than pitch is used to yield a large extinction ratio (e.g., greater than 2). When pitch is greater than or equal to 0.85 μm, the probe beam diameter Dp becomes on the order of the width of the traces, so that eventually there is no transmission of the incident light, and instead there is full reflection.

Thereafter, in one embodiment beam 203t is reflected (thereby to form reflected portion 203r) by a surface (not shown in FIG. 2A) between layer 202 and an underlying layer. Reflected portion 203r passes back between traces 211A-211N in the direction DR that is opposite to the incidence direction DI, and is measured. Perpendicular polarized beam 203i is used in one implementation with an additional pump beam as described in the related patent application, U.S. patent application Ser. No. 09/095,804 to generate charge carriers and a lock-in amplifier-provides a measure of a property of a layer underneath traces 211-211N. In another implementation, reflected portion 203r is used directly (without any additional beam) as an average measure of the thickness of layer 13 across multiple such regions (e.g., in a single wafer).

In another example, a probe beam 204i (FIG. 2A) is polarized parallel to traces 211A-211N, and both beams 203i and 204i are coincident (on the same region 211) and both illuminate the traces 211A-211N. A majority of the energy of beam 204i is reflected by traces 211A-211N, as reflected portion 204r. Reflected portion 204r can be used to determine a property of traces 211A-211N, e.g., by measuring reflectance directly or by measuring interference between the two reflected portions 203r and 204r. Note that a change in reflectance can indicate a corresponding change in grain structure due to change in surface roughness. Roughness can also be measured by measuring light scattering (e.g., as indicated by a ratio of intensity of diffuse and specular reflection). Alternatively, instead of the probe beam 203i, a heating beam can be used as described in the related patent application, U.S. patent application Ser. No. 09/095,805. Specifically, the heating beam has a power (also called "heating power") modulated at a frequency which is selected to be sufficiently small to cause a majority of the heat to transfer by diffusion from region 211. In one example, the heating beam has a wavelength of 0.83 microns, has an average power of 10 milliwatts, a diameter of 2 microns and is modulated at 2000 Hertz.

The modulation frequency of the heating beam is selected to be sufficiently small to ensure that at any time the temperature of traces 211A-211N is approximately equal to (e.g., within 90% of) the temperature of these same traces 211A-211N when heated by an unmodulated beam (i.e., a beam having constant power, equal to the instantaneous power of the modulated beam). For example, the modulation can be sinusoidal between 0 and 50 milliwatts, i.e., P=50 sin (2π ft), where f is the modulation frequency. In such an example, at the time when the modulated power has an instantaneous value of 25 mW, the temperature under the heating beam approximately equals (e.g., is no less than 90% of) the temperature obtained with a heating beam having constant power, e.g., 25 mW.

In one embodiment, the modulation frequency is selected to cause all traces 211A-211N illuminated by the heating beam to be at substantially the same temperature relative to one another (e.g., varying less than 10% between adjacent traces). Such a linear response condition occurs when the thermal wavelength λ (which is the wavelength of a thermal wave that is formed in the structure) is at least an order of magnitude larger than the diameter Dp of the illuminated region 11.

Therefore, when a heating beam is modulated, the temperature T (and therefore the reflectance) of traces 211A-211M is also modulated in phase with modulation of the heating beam (under linear response conditions). Reflected portion 204r (which is sensed to generate an electrical signal) is also modulated, in phase with modulation of the heating beam. The modulated electrical signal is detected by use of a lock-in amplifier as stated in the patent application Ser. No. 098/095,805. The modulated electrical signal can be used to identify variations in one or more material of the traces (e.g., resistance per unit length which is indicative of cross-sectional area). Note that a heating beam and a probe beam can be offset from one another, for example by a distance of 5-8 μm because the effect of the heating beam (the linear thermal response) is noticeable for a greater distance (e.g., 10-15 μm) before reaching room temperature.

Figure 2C:
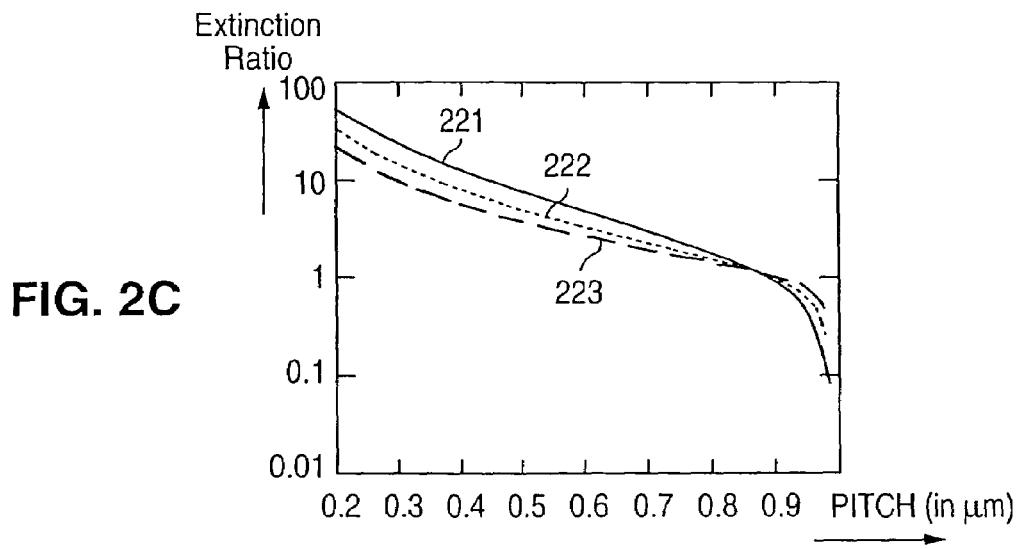
FIG. 2C illustrates, in a graph, relation between pitch (on the x axis) and extinction ratio (on the y axis) for light of a fixed wavelength, wherein the extinction ratio is a ratio of light (intensity) transmitted to a region underneath the traces (FIG. 2A) in the perpendicular and parallel directions.
Figure 2D:
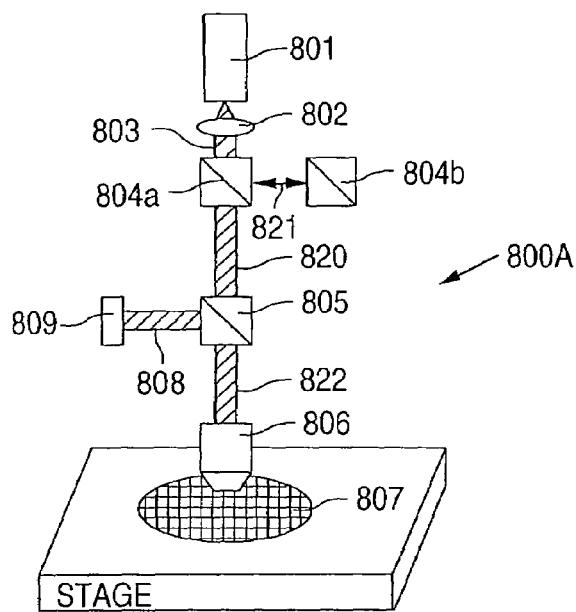
FIGS. 2D, 2E and 2G illustrate, in block diagrams, alternative embodiments that use one or more polarized components of a probe beam.

In one embodiment, an apparatus 800A (FIG. 2D) is used to practice one or more methods described herein. Specifically, apparatus 800A includes a lens 802 that collimates a beam generated by a laser 801, thereby to provide a beam 803. Depending on the implementation, laser 802 can generate a beam that is not polarized, or polarized in a direction 45° relative to the traces. Apparatus 800A includes two polarizers 804a and 804b (such as polarizing beam splitting cubes). Polarizer 804a is located in the path of beam 803, and transmits light polarized in the plane of the paper and deflects light polarized perpendicular to the plane of the paper. Thus beam 820 transmitted by polarizer 804a is polarized in the plane of the paper. A beam 821 that is deflected by polarizer 804a is sent to an absorber (for safe disposal).

Instead of using polarizer 804a, apparatus 800A can be configured to use another polarizer 804b that is located offset from the path of beam 803. Polarizer 804b transmits light polarized perpendicular to the plane of the paper and deflects light in the plane of the paper. Beam 820 is incident on a beam splitter 805 that is also included in apparatus 800a. Beam splitter 805 passes a portion (e.g., 50%) of the incident light as beam 822 which is focused on structure 807 by an objective lens 806 located therebetween. Light reflected from structure 807 is deflected by a beam splitter 805 to form beam 808 which is incident on a detector 809.

In one implementation, the parts described in the following table are used to form apparatus 800A.

801 980 nm laser diode model SDLO-2597-160-BN (Spectra Diode Labs)
802 Collimating lens Thor Labs P/NF230FC-B followed by 3× anamorphic prism, Melles Griot P/N 06GPA004.
804a,b Cube beamsplitter, Part 05FC16PB.7, available from Newport, Irvine, Calif.
805 Cube beamsplitter, Newport P/N 05BC17MB.1
806 100X objective lens, Part 1-LM5951 available from Olympus, Tokyo, Japan.
809 Si PIN photodiode. Hamamatsu S2386-8K
810 Same as 804
812a,b Same as 809

Hamamatsu is in Hamamatsu, Japan. Newport is in Irvine, Calif. Thor Labs is in Newton, N.J. Spectra Diode Labs is in San Jose, Calif.

In addition a Wollaston prism may be inserted (described later). This is made by Karl Lambrecht, part number MWQ12-2.5am-V810. A polarizer may be placed following the Wollaston prism, such as a Polarcor™ Linear Polarizer. Newport P/N05P309AR.16.

Note that polarizers 804a and 804b can be replaced by a half-wave plate located in the path of beam 803 (i.e., inline between lens 803 and beam splitter 805). In this case, laser 801 is polarized. The half-wave plate rotates polarization of beam 803 by 90°, thereby to cause beam 810 to have orthogonal polarization. The half-wave plate performs rotation of polarization to provide a probe beam having polarization in either direction without loss of power (whereas when a beam splitting cube is used, 50% of the power is deflected and lost).

Figure 2E:
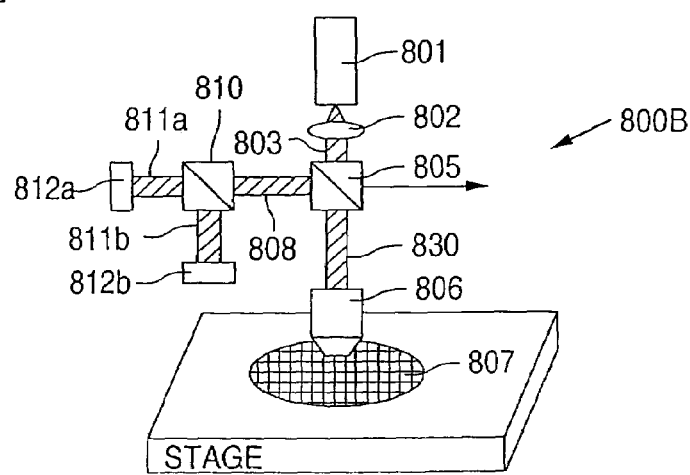

In another embodiment, apparatus 800B (FIG. 2E) includes a laser 801 that generates a beam 803 that is either unpolarized or circularly polarized (thereby containing components in both polarization directions). As described above, beam splitter 805 passes only a portion of beam 803 as beam 830, while another portion 808 is incident on a polarizer 810 (which can be, e.g., a polarizing beam splitter). Note that beam 808 is a return beam from laser 801. When beam 808 is unpolarized or circularly polarized, beam 808 contains components in both polarization directions.

Polarizer 810 passes one polarization component to detector 812a as beam 811a, and deflects the other polarization component as beam 811b to detector 812b. Detectors 812a and 812b simultaneously provide measurements of the individual intensities of beams 811*a* and 811*b* (which represent the parallel and perpendicular polarization directions depending on the orientation of the pattern on the wafer 807 with respect to the orientation of beam splitter 810). Note that a polarizing beam splitter can be included in the apparatus of FIGS. 2D and 2E, between splitter 805 and lens 806. In this case, beam 822 (FIG. 2D) or beam 830 (FIG. 2E) is split into two components having mutually perpendicular polarization directions. As described below, lens 806 focuses the two spatially separated beams on wafer 807 (see FIGS. 6C and 6D). In addition, a polarizer can be included between prism 805 and lens 806. If such a polarizer has its transmission direction oriented at 45° relative to the two polarization directions, then the two spatially separate beams have the same polarization direction (as illustrated in FIGS. 7C and 7D).

One embodiment uses two probe beams that are polarized in the parallel and perpendicular directions relative to traces 211A-211M. In this embodiment, two electrical signals for the two polarization directions are used contemporaneously (e.g., just before, during or just after each other). Depending on the implementation, the two probe beams can originate from a single beam that is either nonpolarized (with the components being obtained after reflection, by passage through a polarizing beam splitter), or is polarized at 45° relative to traces 211A-211M. Alternatively, the two probe beams can originate in two independently generated beams that are polarized in the parallel and perpendicular directions relative to traces 211A-211M.

An electrical signal is obtained by measuring the reflected light when using the above-described two probe beams for a production wafer. Such a signal is used (in this implementation) with charts (which may be in tabular form or graphical form and which are formed by use of wafers having known properties) to look up the average thickness of layer 202 and the average thickness of traces 211A-211N. For example, when beam 12 (FIG. LA) has one of wavelengths 1.48 μm or 0.83 μm, one of respective lines 326 and 327 (FIG. JA) is used to look up average thickness "t" of layer 202 (e.g. in the 0.8-1.2 μm range).

To resolve any ambiguity in a reading from the chart, the measurement can be repeated with probe beam(s) of different wavelengths(s). For example, if when using the 1.48 μm wavelength beam (see line 326 in FIG. 3A), the reflectance signal is 0.2 (ratio of reflected power to incident power; if the incident power is 1 mW and the conversion efficiency is 1 V/mW, then the signal is 0.2 volts) then the thickness can be either 0.885 μm or 1.105 μm. In the example, if when using the 0.83 μm wavelength beam (see line 327 in FIG. 3A), the reflectance signal is 0.3 (ratio of reflected power to incident power, or 0.3 volts with an incident power of 1 mW and conversion efficiency of 1 V/mW) then the thickness is 1.1 μm.

When a beam of electromagnetic radiation falls onto a structure having a number of layers of different materials, multiple reflections take place within the structure. If the distances between the various boundaries are sufficiently small (e.g. less than the ½ the coherence length of the beam) the reflected beams are coherent with one another, and will interfere. Several equations presented below describe properties of such a structure in terms of the reflectance measurements, and can be used to program a computer (as would be apparent to the skilled artisan) to display the properties or change in properties. The structure may consist of l layers. The structure's properties include not only the refractive indexes $n_i$ and the thicknesses $t_i$ of the layers but also the refractive indexes $n_i$ and $n_m$ of the substrate and the transmission medium.

The angle of incidence θ and the wavelength λ and plane of polarization (⊥ or ∥) of the incident radiations are the external to the structure. A method of calculating the transmittance T and the reflectance R of a multilayered structure from the above-described properties is based on a matrix formulation of the boundary conditions of the surfaces (derived from Maxwell's equations). Specifically, it can be shown that the ith layer can be represented by the following 2×2 matrix $$M_j = \begin{bmatrix} \cos(\delta_j) & \frac{i}{u_j}\sin(\delta_j) \\ iu_j\cos(\delta_j) & \cos(\delta_j) \end{bmatrix} \quad (8)$$

$$\text{where } \delta_j = \frac{2\pi}{\lambda}(n_j t_j \cos(\phi_j)) \quad (9)$$

the quantity $n_j t_j \cos \phi_j$ often being called the effective optical thickness of the layer for an angle of refraction $\phi_j$ and where $u_j$, the effective refractive index, is given by $$u_j = \begin{cases} \dfrac{n_j}{\cos(\phi_j)} \\ n_j \cos(\phi_j) \end{cases} \quad (10)$$

depending on whether the incident radiation is polarized parallel (top case of $u_j$ in equation 10) or perpendicular (bottom case of $u_j$ in equation 10) to the plane of incidence.

The angle $\phi_j$ is related to the angle of incidence θ by Snell's law $$n_m \sin \theta = n_j \sin \phi_j \quad (11)$$

The complete multilayered structure is represented by the product matrix M, $$M = M_1 M_2 \ldots M_j \ldots M_{i-1} M_i \quad (12)$$

$$M = \begin{bmatrix} m_{11} & im_{12} \\ im_{21} & m_{22} \end{bmatrix} \quad (13)$$

In the above equations (8)-(13) the refractive index of any absorbing material in the structure must be replaced by its complex refractive index ń, defined by $$ń = n - ik \quad (14)$$

Where k is the extinction coefficient of the material. Even though all the elements of the layer matrix for such a material are now complex, its determinant will still be unity.

In terms of the elements of the product matrix, the amplitude transmittance and reflectance coefficients t and r are given by $$t = \frac{2n_m}{(X+W)+i(Y+V)} \quad (15)$$

$$r = \frac{(X-W)+i(Y-V)}{(X+W)+i(Y+V)} \quad (16)$$

where $$X = n_m m_{11} + n_m k_s m_{12},$$

$$Y = n_m n_s m_{12},$$

$$W = n_s m_{22},$$

$$V = m_{21} - k_s m_{22}, \quad (17)$$

where $m_{ij}$ are the elements of the matrix in equation 8, $n_s - ik_s$ is the complex refractive index of the substrate, and nm is the refractive index of the incident medium, which is usually air, so that $n_m = 1$.

The intensity transmittance and reflectance coefficients are $$T = n_s/n_m |t|^2 \quad (18)$$

$$R = |r|^2 \quad (19)$$

The absorption of a multilayer is calculated from $$A = 1 - T - R \quad (20)$$

Figure 1B:
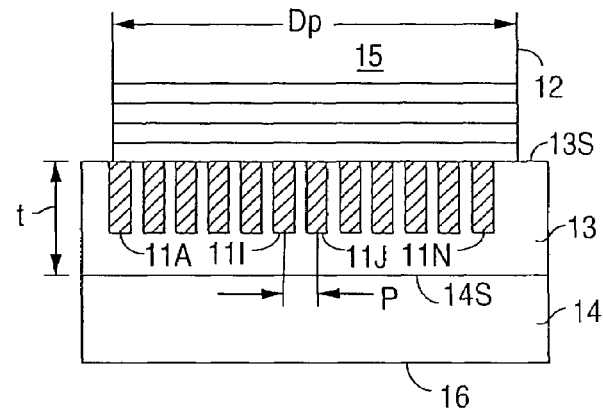
FIG. 1B illustrates, in an elevation view in the direction 1B of FIG. 1A, the relationship between the diameter Dp of the probe beam and the pitch p between the traces.
Figure 1C:
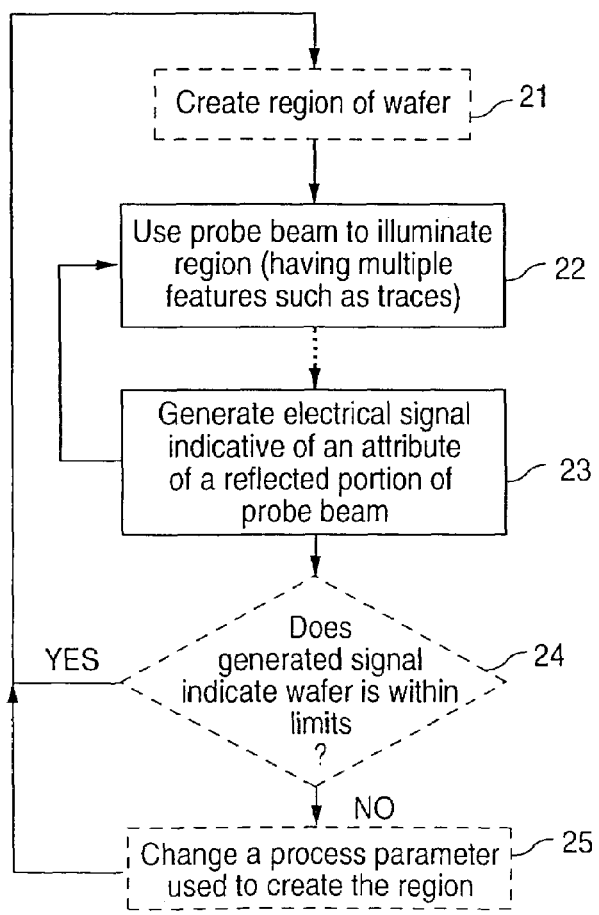
FIG. 1C illustrates, in a flow chart, acts (including illumination of multiple traces illustrated in FIGS. 1A and 1B) being performed during wafer fabrication, in one embodiment of the invention.
Figure 2F:
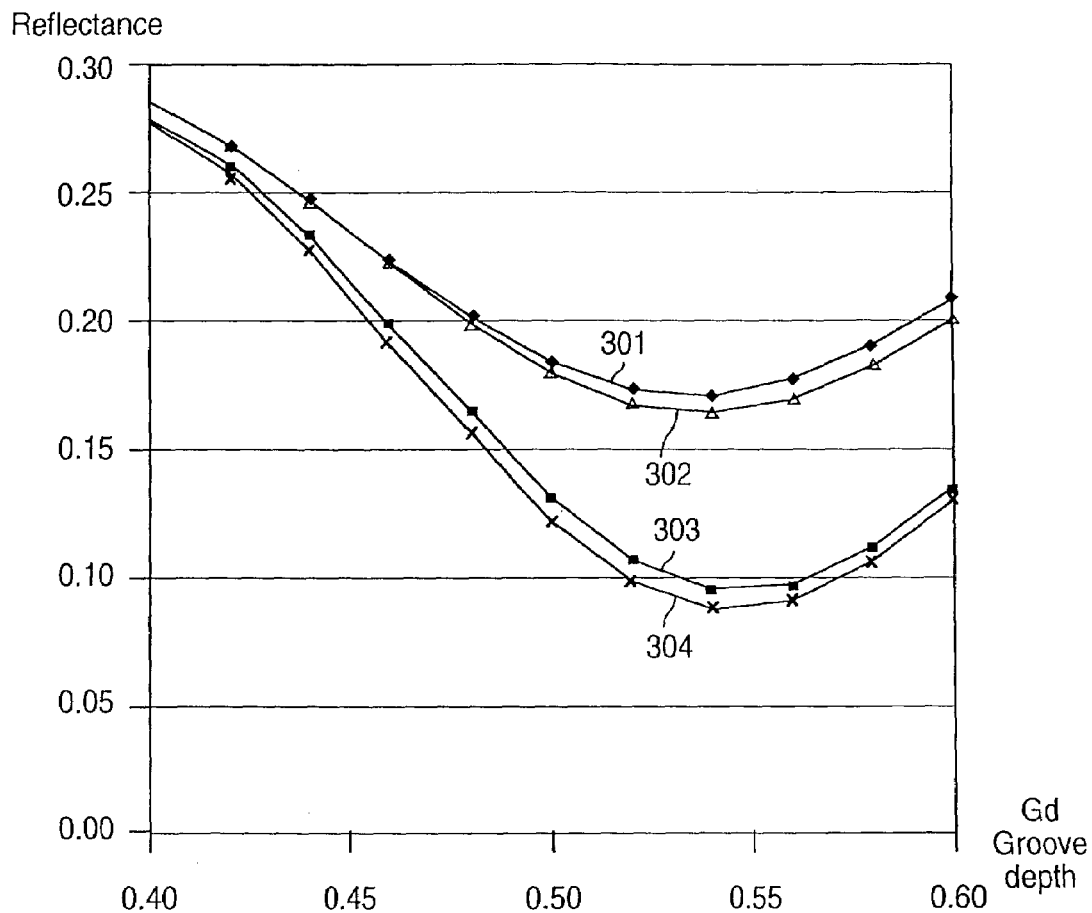
FIG. 2F illustrates, in a graph, the change in reflectance of the structure of FIG. 2B as a function of depth Gd of the grooves.

Note that lines 326 and 327 (FIG. 3A) are for use when a single beam 12 (FIG. 1A) is incident on region 11 and includes light polarized perpendicular as well as parallel to traces 11A-11N (FIG. 1A). Each polarization direction of light reflected from region 11 may include two components (reflected by each of surfaces 13s and 14s) that interfere. Two such measurements of reflectance using probe beams of the two wavelengths when used with lines 326 and 327 determine a unique value of thickness of layer 13. Note that pitch "p" is less than half the smallest wavelength, i.e., p<0.5 µm. Note that if such parallel and perpendicular polarized probe beams are offset from one another, a surface profile is obtained from the reflected signal as discussed below.

Figure 3B:
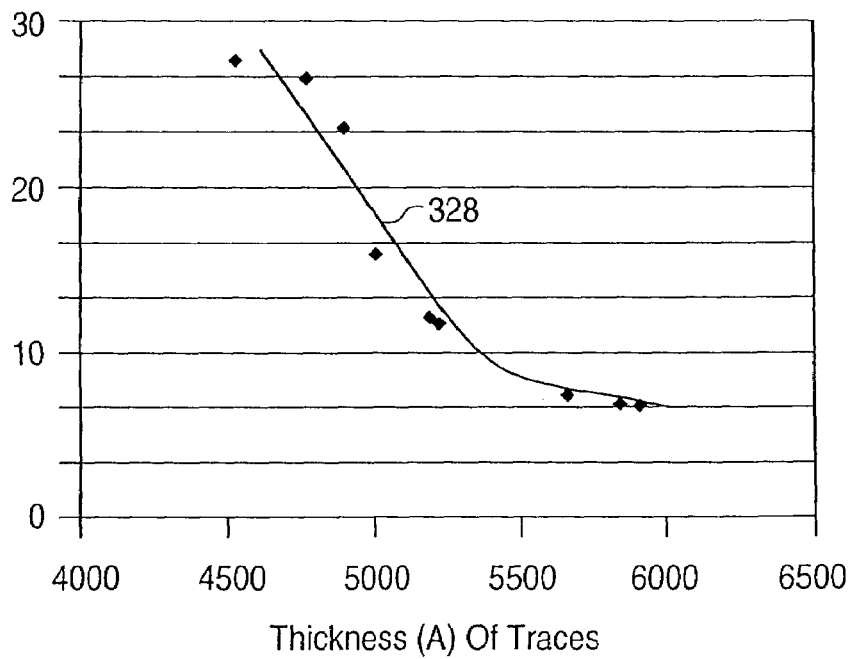

In a similar manner, another line 328 (FIG. 3B) is used to look up average thickness "m" of traces 211A-211N (FIG. 2A) in the illuminated region. In the example illustrated in FIG. 3B, a reflectance signal is plotted on the y axis and thickness of traces (in the form of traces in a semiconductor substrate) is plotted along the x axis. In this example, pitch p is 0.36 µm and trace width is 0.18 µm.

Note that the thickness of traces 211A-211N can also be determined from a measure of resistance per unit length (e.g., as described in Ser. No. 09/095,05), which indicates cross-sectional area if the line width and conductivity are both substantially fixed (e.g., change less than 10% in the illuminated region).

Figure 3C:
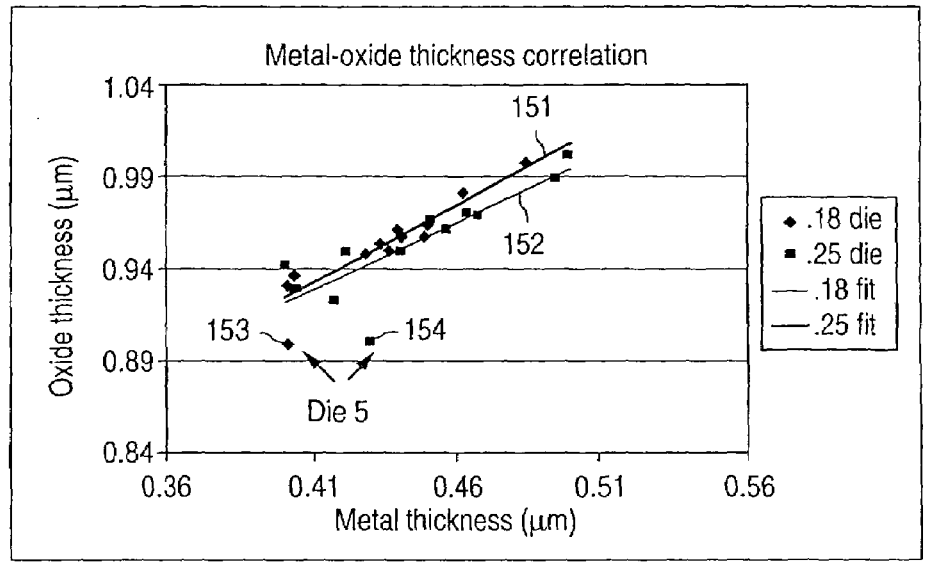
Figure 3D:
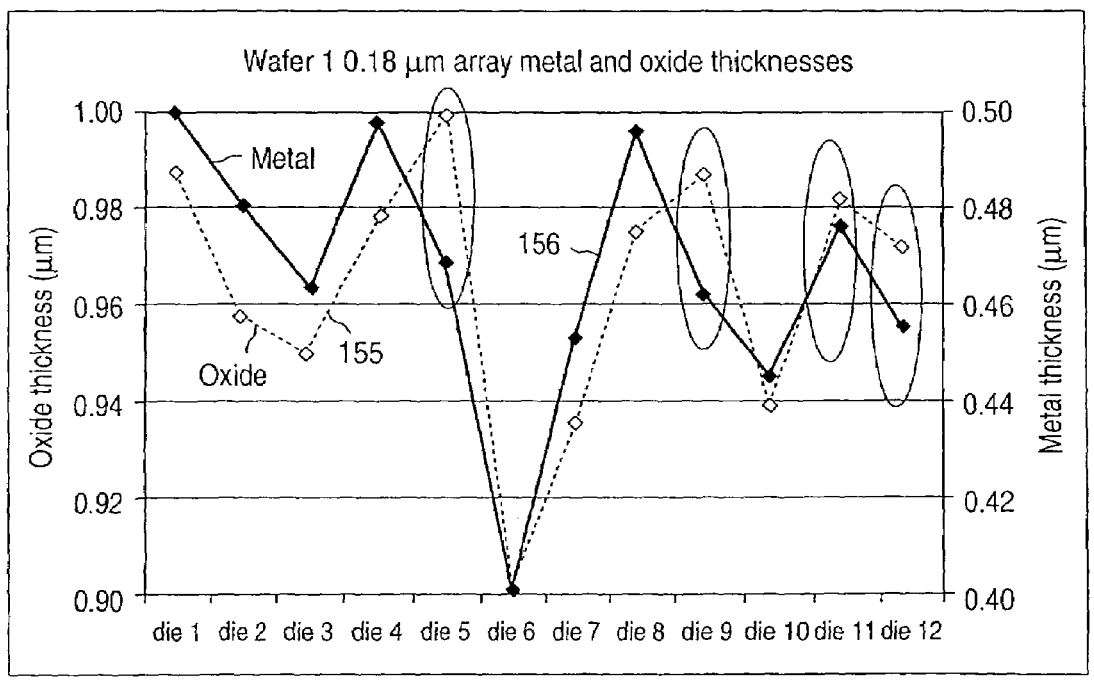

In this embodiment, the measurements are repeated at multiple dice in a production wafer, and the thickness values are plotted for the various dice as illustrated in FIGS. 3C-3E. For example, a graph with the thickness of layer 202 plotted along the x axis, and the thickness of traces 211A-211N plotted along they axis results in points that fall along a straight line. For example, lines 151 and 152 (FIG. 3C) are fitted to the points plotted for 0.18 µm and 0.25 µm dice respectively.

In the just described example, 0.18 µm and 0.25 µm are half-pitches (e.g., same as trace width, with trace width equal to the space between the traces) so that pitch is 0.36 and 0.5 µm respectively. Note that the measurements illustrated in FIG. 3C are obtained by use of a heating beam to measure thickness m of traces 211A-211N, and by use of interference to measure thickness t of layer 202 as described herein. Note, however that points 153 and 154 for die 5 are at a significant distance from lines 151 and 152 thereby to indicate a problem with the width of traces 211A-211M in die 5.

Instead of fitting the thickness measurements to a line, the thickness measurements can be plotted along the y axis, with the x axis representing the various dice as illustrated in FIG. 3D. Note that the relationship between the two lines 155 and 156 reverses for each of dice 5, 9, 11 and 12, thereby to indicate a problem with line width in these dice. Note that the difference between the two thickness measurements can also be plotted as illustrated in FIG. 3E. A difference in excess of a control limit (e.g., 0.50) indicates a problem.

Therefore, in one embodiment, the various graphs in FIGS. 3A-3E indicate a problem if there is a discontinuity therein. Instead of, or in addition to comparing the thicknesses relative to one another, each thickness can be compared to a range of acceptable thicknesses. When thickness falls outside the range, there is a problem (e.g., over or under polishing or metal deposition problem). Simultaneous generation of the two electrical signals for the two thicknesses provides an advantage in speed, as compared to sequential generation of the two signals.

Instead of determining the absolute value of thicknesses "t" and "m" as described above, the measurements can be directly plotted (or compared to a range) to identify variation in the measurements. When the variation exceeds a predetermined limit, appropriate acts are performed to correct the situation (e.g., by changing a process parameter used to control fabrication of another wafer). Therefore, reflectance need not be computed, and instead a signal indicative of intensity of a reflected portion is used directly.

In one embodiment, a method 400 (FIG. 4A) uses two signals of the type described above to evaluate a wafer as follows. Specifically, in act 310, a wafer is inserted into a wafer aligner of apparatus 125, and traces formed therein are oriented in a predetermined direction relative to a stage. Next, in act 301, one or more polarized beams having a known orientation relative to the predetermined direction (i.e., relative to the traces) are generated, and illuminate the traces. Thereafter, in act 302, a property of the array of traces is measured, using a beam polarized parallel to the traces. Computer 126 checks if the measured property is within a predetermined range, and if not a process parameter is adjusted (e.g., via bus 115 described above) as illustrated by act 302a.

Then, in act 303, a property of the layer in which the array of traces is embedded is measured, using a beam polarized perpendicular to the traces. Computer 126 checks (in act 303) if the measured property is within a predetermined range, and if not another process parameter (or even the same process parameter described above) is adjusted, as illustrated by act 303a. Next, computer 126 compares (in act 304) the two measurements to one another, and if there is a large deviation yet another process parameter (or even the same parameter) is adjusted, as illustrated by act 304a. Then the above-described acts are repeated (in act 305) at a number of sites, to obtain a uniformity map of the type illustrated in FIGS. 3C-3E.

Figure 4B:
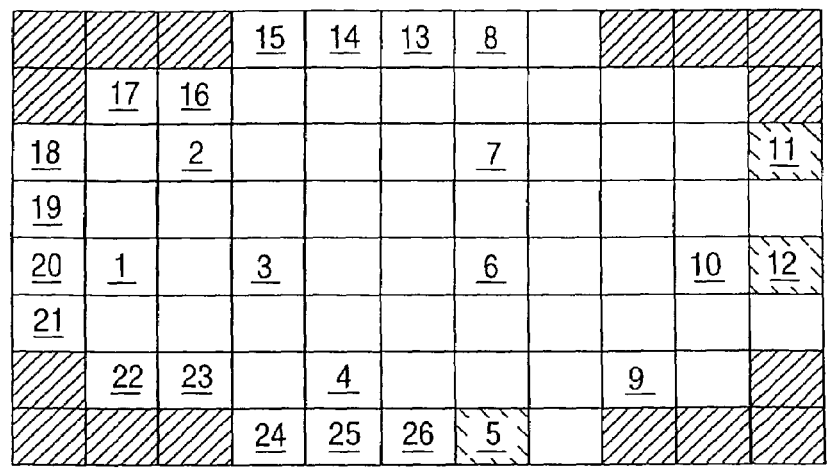
FIG. 4B illustrates variations in measurements across a wafer in one example of a uniformity map obtained towards the end of the process illustrated in FIG. 4A.

Note that the measurements can also be displayed to an operation (by computer 126) in a two-dimensional map of the wafer as illustrated in FIG. 4B. For example, dies 5, 9, 11 and 12 may be shown highlighted (e.g., brightened, darkened or different color or hatched) to indicate measurements beyond a control limit (see FIG. 3E). There may be different types of highlighting (e.g., die 5 v/s dies 9, 11, 12) to show the degree of variation beyond the control limit. Instead of using a control limit, all measurements may be displayed (in correspondingly varying shades of gray or color).

Such two-dimensional maps indicate variations across the production wafer (e.g., dies 5, 9, 11 and 12) are located at the periphery of the wafer and therefore indicate a problem at the periphery. An example of such a problem could occur due to voids forming in the metal traces, typically if dies all around the periphery fall outside of a control limit (in the example dies 13-26 may fall with the control limit and so a different problem may be present). If several dies of a particular region (e.g., dies 5, 9, 11 and 12 in the bottom right corner) are affected, there may be a problem in that region, such as a number of voids in one or more of the traces in the illuminated region.

If the uniformity is not within control limits, a process parameter is adjusted, as illustrated by act 305a. If a production wafer passes all the tests, one or more additional layers are formed on the wafer by the various apparatuses 120-124 (FIG. 1D), and then the wafer is returned to the aligner (in act 310), and the measurement and control acts 301-305 are repeated. Note that while forming the additional layers, acts 301-305 and 310 can be performed on a different production wafer.

Figure 1D:
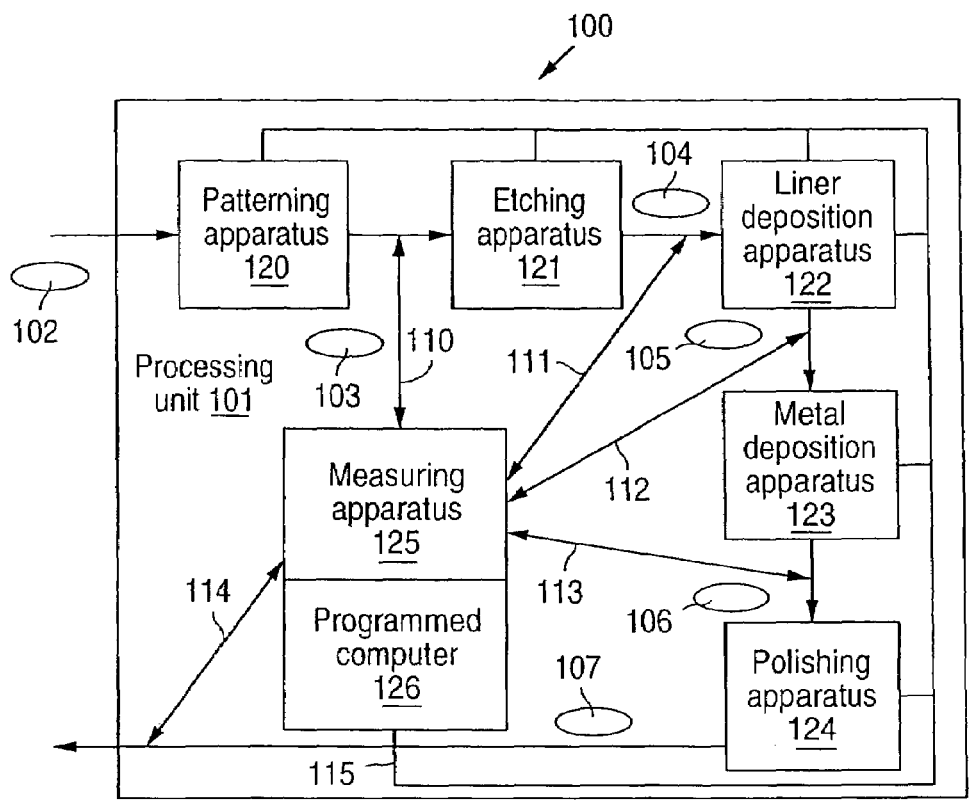
FIG. 1D illustrates, in a block diagram, one embodiment of a measurement apparatus of this invention being used with various devices that fabricate the structure of FIG. 1A.
Figure 1K:
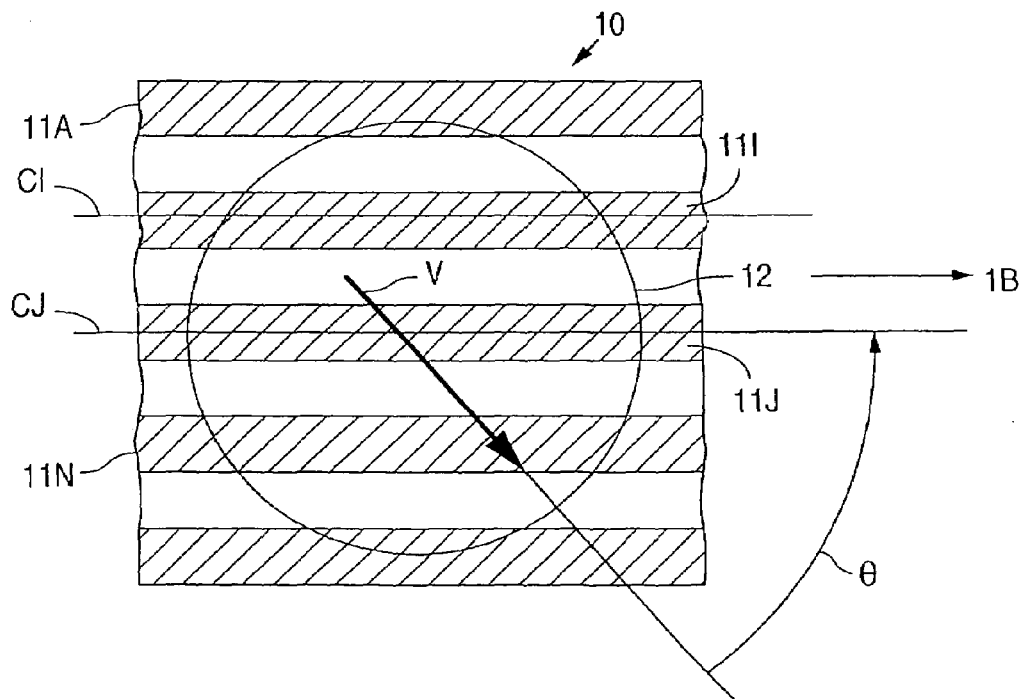
FIG. 1K illustrates, in a plan view of the arrangement illustrated in FIG. 1A, the relation between the electric field vector (of a probe beam that is linearly polarized) and the traces.
Figure 5A:
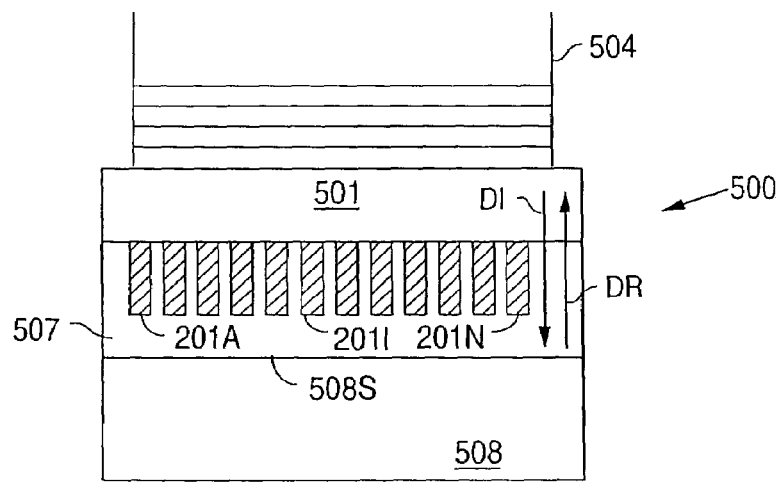
FIGS. 5A and 5B illustrate, in partial cross-sectional views, measurement of properties of a semiconductor wafer having an exposed layer formed on traces in two variants.

In several of the above-described embodiments, there is a transmissive medium directly in contact with the traces, between the traces (on the structure) and a source of the beam. However, in another embodiment, a substrate 500 (FIG. 5A) has a transmissive layer (e.g., oxide) 501 formed over a network of traces 201A-201N, and layer 501 is evaluated by measurement apparatus 125 (FIG. 1D). One or more properties of layer 501 are measured by use of a probe beam polarized in a direction parallel to traces 201A-201N, a portion of the probe beam being reflected from underneath layer 501, by traces 201A-201N.

In one variant of the just-described example, a heating beam 504 is used in addition to the above-described probe beam. Heating beam 504 can be polarized parallel to the traces, for heating the traces as described above. Alternatively, heating beam 504 can be polarized perpendicular to traces 201A-201N, and therefore passes through layer 507 twice, once in the incidence direction DI, and a second time in the opposite direction DR after reflection by surface 508s between layers 507 and 508. So beam 504 which covers multiple traces 201A-201N provides an increased heating effect (as compared to a heating beam that is incident only on one trace 201I or incident polarized parallel to traces 201A-201N).

Note that the just-described increased heating effect depends on several factors such as thickness of traces 201A-201N, the direction of polarization relative to the longitudinal direction of traces 201A-201N, and the thickness of layer 507 (which affects the reflected power from the underlying structure). In another embodiment, the heating beam is polarized parallel to the longitudinal direction of the traces. In this case, the heating is independent of the thickness of the traces or of the thickness of layer 507. This provides heating independent of other parameters of the structure e.g., if measuring resistance per unit length.

Therefore, the extinction ratio (FIG. 2C) changes with change in thickness of traces 201A-201N. If the width of traces 201A-201N is fixed, the extinction ratio can be used as a measure of the trace thickness. If trace thickness is fixed, then the extinction ratio provides a measure of variation in thickness of layer 507. In one implementation, a measurement (using a probe beam and heating beam 504) is made immediately after formation of layer 501, and provides a more immediate feedback to control the operation of the apparatus (FIG. 1D) used to form layer 501.

Figure 5B:
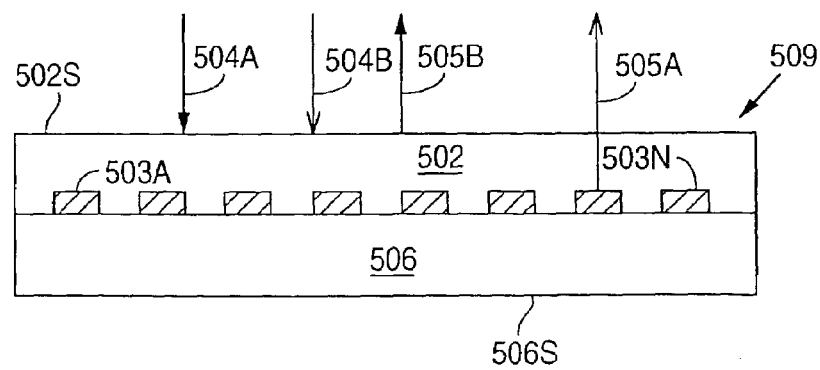

Note that depending on the embodiment, layer 501 (FIG. 5A) can be in contact with just one surface of each of traces 201A-201N, or alternatively a layer 502 (FIG. 5B) can be in contact with multiple surfaces (e.g., three surfaces) of each of traces 201A-201N (e.g., traces 201A-201N are embedded in layer 502). In one embodiment, two probe beams 504A and 504B (FIG. 5B) that are polarized in mutually perpendicular directions (e.g., obtained by use of a Wollaston prism) are used to evaluate a structure 509 having traces 503A-503N that are embedded within a layer 502. In this embodiment, beam 504A that is polarized parallel to traces 503A-503N is reflected as beam 505A by these traces, and interferes with a beam 505B which is a portion of perpendicular polarized beam 504B reflected by surface 502S (assuming that layer 506 is a substrate that absorbs light). The two reflected beams 505A and 505B interfere, and an electrical signal derived therefrom provides a profile of traces 503A-503N.

Figure 6A:
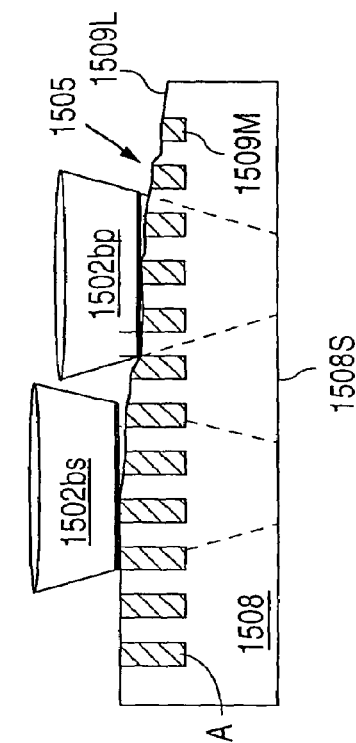
FIGS. 6A and 6B illustrate, in cross-sectional views, two mutually perpendicular components of a probe beam that are offset from one another for use in obtaining a surface profile.
Figure 6B:
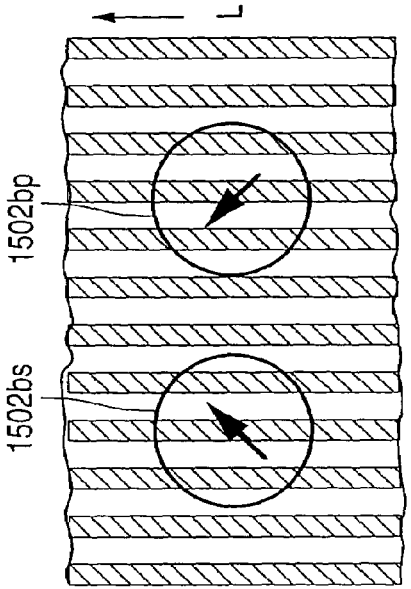
Figure 6C:
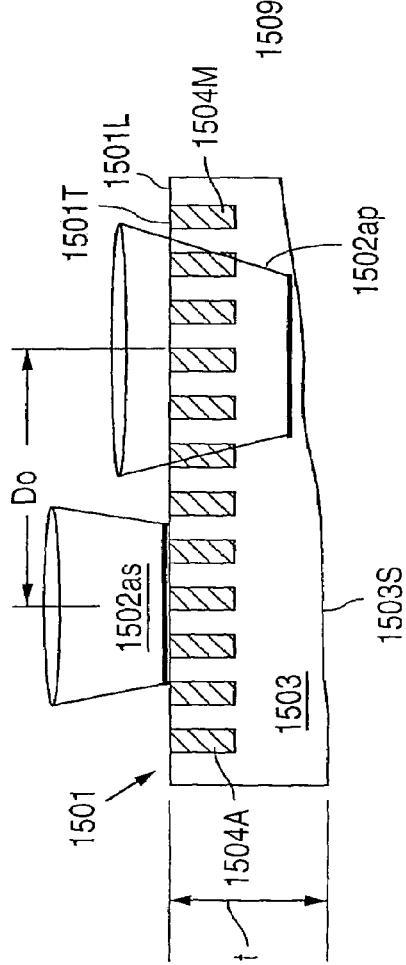
FIGS. 6C and 6D illustrate, in plan views, the orientation of polarization direction of the beams of FIGS. 6A and 6B respectively relative to the traces.
Figure 6D:
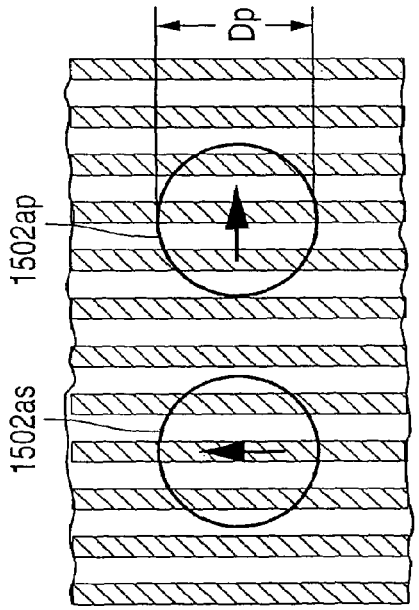

In another embodiment, two beams polarized perpendicular to each other are used with structure 1501 that has traces 1504A-1504M exposed to the transmissive medium. In this embodiment, a portion of the parallel polarized beam 1502as (FIG. 6A) is reflected by traces 1504A-1504M, and a portion of the perpendicular polarized beam 1502ap (FIG. 6C) is reflected from a surface 1503S of layer 1503 underneath traces 1504A-1504M. Note that traces 1504A-1504M are coplanar as illustrated in FIG. 6A, while the similar traces 1509A-1509M are substantially coplanar as illustrated in FIG. 6B (e.g., the "substantially coplanar" traces may be embedded in the same layer 1508 to form a single exposed surface 1509L).

In the preceding sentence, the terms "coplanar" and "substantially coplanar" are used to mean the following. In the case of coplanar, the surface serves as a reference to measure the profile of the underlying surface. Hence, the planarity of lines 1504A-M should be less than 10% of the profile of surface 1503S. Substantially coplanar refers to the profile of surface 1509L, which could be defined as an order of magnitude less planar than underlying reference surface 1508S.

The reflected portions are used to generate an electrical signal which indicates a profile of the underneath surface 1503S when the beams 1502as and 1502ap are offset by a distance Do. Offset distance Do may be, for example same as a diameter Dp of probe beam at the illuminated regions. When the two polarized beams are coincident on the same region (e.g. see region 11 illustrated in FIG. 1A), such an electrical signal indicates a thickness t of the exposed layer(e.g. layer 1503 in FIG. 6A).

Figure 6E:
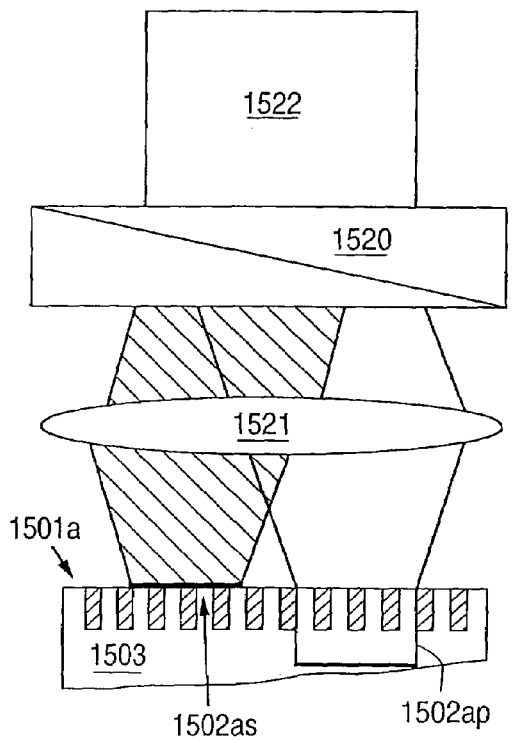
FIG. 6E illustrates use of a polarizing beam splitter 1520 to generate the two components of the probe beam illustrated in FIGS. 6C and 6D.

Note that in structure 1501, exposed surface 1501T of a trace 1504M is co-planar with a surface 1501L of a layer that interdigitates between the traces 1504A-1504M, and these two surfaces can be formed, e.g., by chemical mechanical polishing. The two probe beams 1502as and 1502ap can be generated in any manner, by use of a polarizing optical element such as a Wollaston beam splitting prism and an objective lens focusing the beams on the structure, e.g., as illustrated in FIG. 6E. Note that an exposed surface (formed by surfaces 1501T and 1501L) is being used as a reference surface by the parallel polarized beam (and conversely the surface 1503S can be used as a reference surface by a perpendicularly polarized beam).

Two probe beams 1502bs and 1502bp that are polarized mutually perpendicular to each other can each be oriented at 45° relative to the longitudinal direction L (FIG. 6D) of traces 1509A-1509M, so that at least a portion of each beam is reflected from the exposed surface 1505 (FIG. 6B) of the structure. In such a case, the electrical signal obtained from two or more reflected portions indicates a profile of the exposed surface 1505. An optional polarizing beam splitter can be used to limit the measurement to just the two portions that are reflected by traces 1509A-1509M (as opposed to other portions that may be reflected, e.g. by the underneath surface 1508S.

Figure 7E:
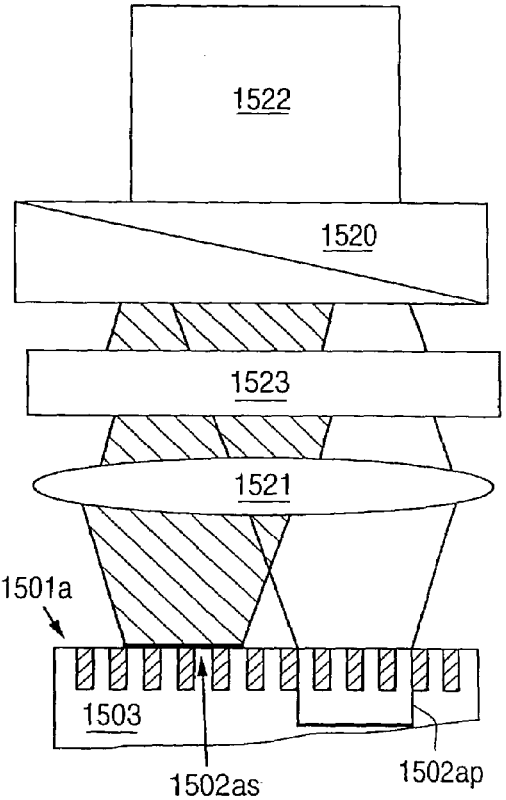

Note that for convenience, FIGS. 7A-7E are labeled with many of the same reference numerals as FIGS. 6A-6E. In one embodiment, a polarizer 1523 (FIG. 7E) is interposed between Wollaston prism 1520 and lens 1521 and is oriented at 45° relative to the two orthogonal polarization directions of beams 1502as and 1502ap generated by prism 1520, so that these beams have polarization directions parallel to one another when incident on lens 1521. For example, as illustrated in FIGS. 7A and 7C, both beams 1502as and 1502ap can be oriented perpendicular to traces 1504A-1504M so that the reflected signal provides a measure of the profile of surface 1503S located underneath traces 1504A-1504M. Alternatively, as illustrated in FIGS. 7B and 7D, both beams 1502bs and 1502bp can be oriented parallel to traces 1509A-1509M, so that the reflected signal provides a measure of the profile of surface 1509L which is formed by traces 1509A-1509M and layer 1508 interdigitating therebetween.

In one specific implementation, the following three techniques are used to perform a number of measurements. In a first technique called "Metal Illumination" (MI), one laser heats a metal film under linear response conditions so that the film's temperature is modulated at a frequency which is selected to be sufficiently small to cause a majority of the heat to transfer by diffusion. The peak temperature is under the beam focal spot, and is a function of the thermal conductivity and cross-section (for a line) or thickness (for a film). A second laser measures the reflectance, which is a function of the surface temperature. If the conductivity is well controlled, the MI measurement correlates to the line cross-section or film thickness. It is typically applicable to films>300 Å thick. The heating beam is normally the 830 nm laser, which may be linearly or circularly polarized.

A second technique called "Polarized Infrared DC Reflectance" (PIR) measures the reflectance of a polarized, normal incidence laser beam. Apparatus 125 (FIG. 1D) has lasers of two wavelengths available: 830 and 980 nm. The 830 nm beam is circularly polarized and the 980 nm beam is unpolarized. Polarization directions are selected using the polarizing beam splitter in the detector, or through the use of a polarizer flipped into the beam to select a polarization from the circularly polarized beam.

A third technique called "Interferometric Surface Profiling" (SP) measures the phase shift between two closely spaced beams with orthogonal or like polarization. This provides a measure of the height difference of the surface at the focus, thereby measuring the local slope. Integrating the slope over the length of a scan comprised of measurements at a number of sites provides the surface profile.

Figure 8:
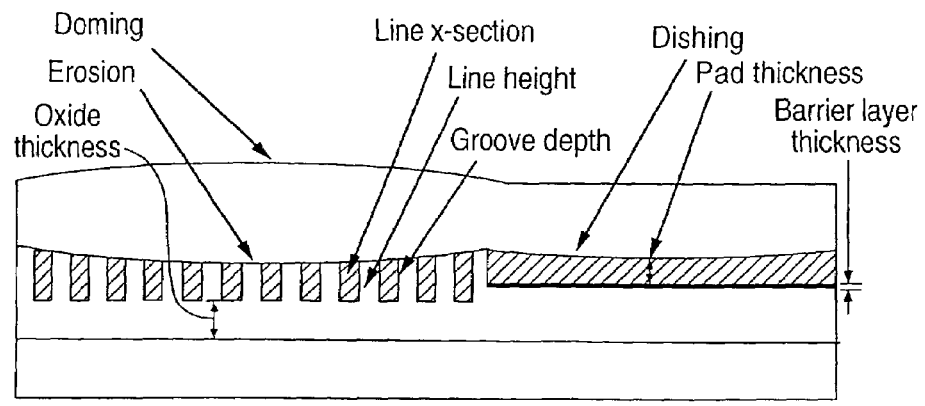
FIG. 8 illustrates, in a partial cross-sectional view, the various defects in a semiconductor wafer that can be identified by use of the measurements described herein.

The measurements are in general applied to damascene structures, although they may be used with conventional metal layers as well. The various defects of a structure that can be identified by the measurements described herein include (see FIG. 8) doming, erosion, oxide thickness, trace cross-section, trace thickness, groove depth, pad thickness, dishing, barrier thickness, etc which are described below in detail.

Doming (via PIR): The pattern dependent thickness variation of an insulator layer left after polishing of the insulator layer, appearing as a domed layer above the array.

Erosion (via SP or MI): The pattern dependent line thickness variation in the fine-line array area, appearing as a depressed region in the middle of the array.

Oxide thickness (via PIR): The thickness of an insulator layer as measured from the surface of the underlying layer to the surface of the insulator.

Line cross-section (via MI): The cross-section area of an individual trace (height×width).

Line height (via PIR & MI): The distance from the top to bottom of an individual trace.

Groove depth (via PIR): The depth of the groove in the insulating layer. The conductive trace is formed within the groove.

Dishing (via MI or SP): The depression in the surface of a pad region after polishing.

Pad thickness (via MI): The thickness of the conductive layer in the pad region.

Barrier thickness (via MI): The thickness of the thin layer formed between the pad and the insulator. The barrier also exists between the lines and the insulator in the arrays.

Post electrodeposition topography (via SP): Before polishing, a conductive layer covers the entire surface. This layer is polished off, leaving the lines and pads. The surface has a topography that is pattern dependent.

Thin layers (via PIR): A variety of thin layers may be used in the process. When thinner than e.g. 400 Å, these layers may be transparent. They are used for barriers, silicides, anti-reflection coatings, and other applications.

Resistance per unit length (line cross-section) (via MI): The MI measurement is used to characterize the cross-section of fine patterned traces. Assuming the conductivity of the material of the trace is constant, the output is resistance per unit length, which varies inversely with the line cross-section. Because the cross-section is the product of the width and height of the trace, comparing the results of this measurement to a thickness measurement will give variation in width. A number of factors can cause width variation, including changes in critical dimensions (CDs), voiding, and barrier thickness. The measurement is also sensitive to adhesion, since it relies on thermal leakage into the surrounding insulator.

For performing the MI measurement, the heating and probing beams are polarized along the length of the traces to eliminate sensitivity to the underlying insulating layer. In this case, the measurement can be performed at any level of metal as long as the pitch is less than the wavelength or the trace width is greater than the spot size (i.e. beam diameter). One, embodiment has a sensitivity requirement of cross-section variation<5%.

Numerous modifications and adaptations of the above-described embodiments, implementations, and examples will become apparent to a person skilled in the art of using lasers to measure properties of semiconductor wafers. For example, in an alternative embodiment, instead of using a laser to generate heating beam 101, another heat source (such as an electron gun and electron focusing column that forms an electron beam) is used to modulate the temperature T. Also, a probe beam used to measure the average trace thickness as described herein can consist of x-rays, in which case there is no need for the wavelength to be longer than the pitch.

Note that the above-described method and apparatus can be used with traces of any metal (such as copper or aluminum) or any silicide (such as titanium, cobalt, or platinum), irrespective of whether or not the traces have been annealed.

Moreover, instead of various shades of grey or color in a map, a contour map may be displayed, with contour lines connecting dies having approximately the same measurements. For example, dies 2, 4, 7 and 8 that fall within the range 0.47-0.48 illustrated in FIG. 3E may be shown connected by a first contour line (or color), dies 1 and 3 maybe shown connected by a second contour lie, dies 6 and 10 may be shown connected by a third contour line, and so-on.

Note that a measure of thickness of a conductive layer as described herein can be used to obtain a surface profile of the conductive layer, e.g., to identify a dimple that may be formed during polishing.

Another embodiment of a method and apparatus of the type described herein illuminates a region of a wafer (having a number of traces over an underlying layer of the type illustrated in FIG. 1A) with polarized white light, and measures the color of the reflected light, e.g. with a camera (and optionally an image processor). Films (such as layer 13 in FIG 1A) that are sufficiently thin (e.g. about 1-2 μm thick) have a reflectance that is a function of wavelength, and therefore reflect light of a color that depends on the thickness (e.g. thickness t in FIG. 1A).

When the incident light is polarized so that the electric field is oriented across the traces, the polarization removes at least some of the effect of the overlying traces (e.g. traces 11A-11N in FIG. 1A) depending on the orientation. Therefore, when using light polarized perpendicular to the longitudinal direction of the traces, only a colored region is seen whose color varies with thickness of the underlying film. The following table indicates the change in color of the reflected light as a function of thickness of the underlying layer.

| Film Thickness (μm) | Color of reflected light |
| --- | --- |
| 0.05 | Tan |
| 0.07 | Brown |
| 0.10 | Dark violet to red violet |
| 0.12 | Royal blue |
| 0.15 | Light blue to metallic blue |
| 0.17 | Metallic to very light yellow green |
| 0.20 | Light gold or yellow slightly metallic |
| 0.22 | Gold with slight yellow orange |
| 0.25 | Orange to melon |
| 0.27 | Red violet |
| 0.30 | Blue to violet blue |
| 0.31 | Blue |
| 0.32 | Blue to blue green |
| 0.34 | Light green |
| 0.35 | Green to yellow green |
| 0.36 | Yellow green |
| 0.37 | Green yellow |
| 0.39 | Yellow |
| 0.41 | Light orange |
| 0.42 | Carnation pink |
| 0.44 | Violet red |
| 0.46 | Red violet |
| 0.47 | Violet |
| 0.48 | Blue violet |
| 0.49 | Blue |
| 0.50 | Blue green |
| 0.52 | Green (broad) |
| 0.54 | Yellow green |
| 0.56 | Green yellow |
| 0.57 | Yellow to "yellowish" (not yellow but is in the position where yellow is to be expected. At times it appears to be light creamy gray or metallic) |
| 0.58 | Light orange or yellow to pink borderline |
| 0.60 | Carnation pink |
| 0.63 | Violet red |
| 0.68 | "Bluish" (Not blue but borderline between violet and blue green. It appears more like a mixture between violet red and blue green and looks grayish) |
| 0.72 | Blue green to green (quite broad) |
| 0.77 | "yellowish" |
| 0.80 | Orange (rather broad for orange |
| 0.82 | Salmon |
| 0.85 | Dull, light red violet |
| 0.86 | Violet |
| 0.87 | Blue violet |
| 0.89 | Blue |
| 0.92 | Blue green |
| 0.95 | Dull yellow green |
| 0.97 | Yellow to "yellowish" |
| 0.99 | Orange |
| 1.00 | Carnation pink |
| 1.02 | Violet red |
| 1.05 | Red violet |
| 1.06 | Violet |
| 1.07 | Blue violet |
| 1.10 | Green |
| 1.11 | Yellow green |
| 1.12 | Green |
| 1.18 | Violet |
| 1.19 | Red violet |
| 1.21 | Violet red |
| 1.24 | Carnation pink to salmon |
| 1.25 | Orange |
| 1.28 | "Yellowish" |
| 1.33 | Sky blue to green blue |
| 1.40 | Orange |
| 1.45 | Violet |
| 1.46 | Blue violet |
| 1.50 | Blue |
| 1.54 | Dull yellow green |

Figure 2G:
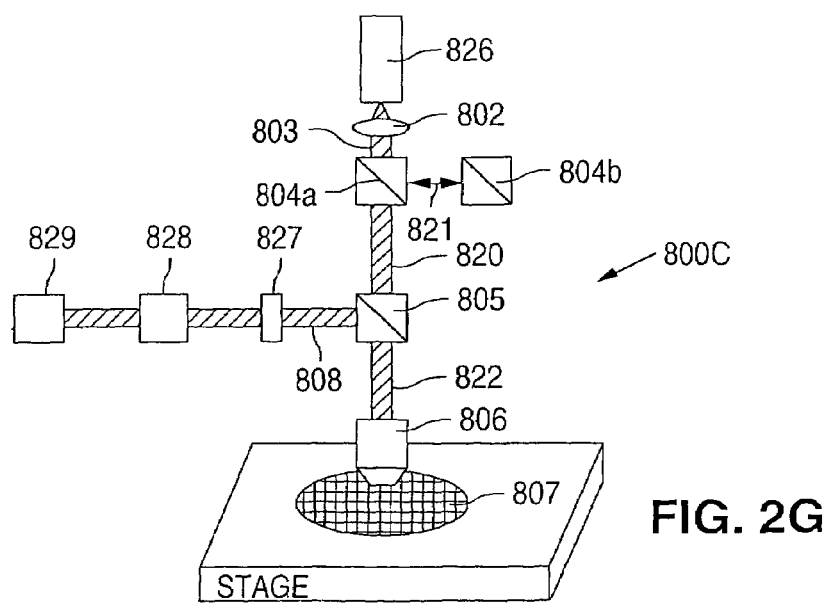

A method that measures the color of reflected light may be performed as follows. A beam of white light generated by a white light source(such as a halogen lamp) 826 (FIG. 2G) is polarized by a polarizer 804a to obtain a beam of polarized white light. Apparatus 800C illustrated in FIG. 2G has many of the same components as apparatus 800A of FIG. 2D. Therefore, many of the reference numerals in FIG. 2G are same as the reference numerals in FIG. 2D, to denote the same components. Note however, that instead of a source of monochromatic light 801 in apparatus 800A, a source of white light 826 is used in apparatus 800C.

The polarized white light from polarizer 804a is used to illuminate a region of structure 807 with the polarization perpendicular to traces on structure 807. Thereafter, a color of a portion of light reflected from structure 807 is measured, e.g. by use of an eyepiece lens 827, a camera 828, and optionally a vision system 829.

Once the color is measured (either by human observation or by an optical instrument), the above table is used with the measured color to look up the thickness t. In a variant of the method, instead of looking up thickness (which is an absolute value), a relative difference in thickness is measured (either qualitatively or quantitatively) by comparing the colors obtained from two (or more) different regions of structure 807, thereby to obtain a corresponding change in thickness of the layer underlying the traces.

Figure 9:
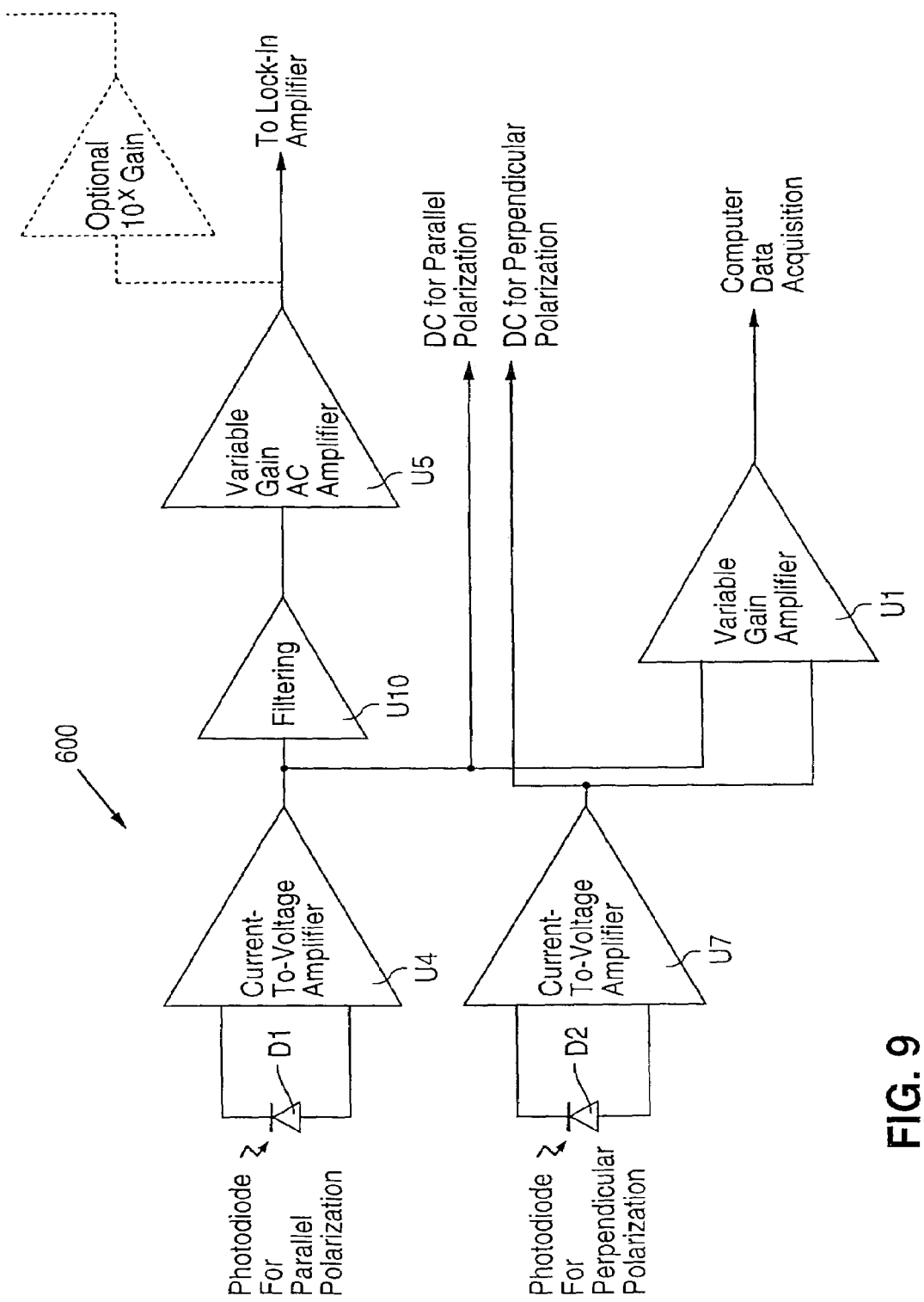
FIG. 9 illustrates, in a high-level block diagram, a circuit included in measurement apparatus 125 of FIG. 1D in one embodiment.

In one implementation, one or more measurements of the type described herein are made by a circuit 600 (FIG. 9) that uses a photodiode (e.g. either of diodes D1 and D2 to generate a current (e.g. 1-2 milli amps) in response to the intensity of light incident on the photodiode. Thereafter, an amplifier U4 (FIG. 9) converts the current from the photodiode into a voltage (e.g. 2-4 volts). Amplifier U4 is coupled to a filter U10 that filters out high frequency noise (e.g. from power lines; e.g. U10 may suppress any signal outside the frequency range 100 Hz to 5 KHz).

Thereafter, an amplifier U11 amplifies the varying component (also called "ac" component) of a measured signal by a gain that is selectable by the user (e.g. the gain may be any one of 1, 2, 4, 8, 16, 32, 64 and 128). The gain may be selected by the user depending on the structure 807 (FIG. 8) that is currently under examination, and the type of signals being obtained from the measurement. If necessary, an optional 10×gain amplifier may be used to further amplify the measured signal. The resulting signal is provided to a lock-in amplifier for processing as described herein.

In another implementation, a signal from another photodiode D2 is amplified (as described above, but by amplifier U7). In addition to summing the measured signals, these signals can be compared to one another, e.g. by an amplifier U1 which provides a difference signal. The difference signal is proportional to a property of the wafer, such as surface roughness.

In an alternative implementation, signals from each of amplifiers U4 and U7 are supplied to a summer (not shown) that in turn provides to filter U10 a signal that is the sum of the two signals obtained from the two photodiodes D1 and D2, for use as described herein.

Numerous modifications and adaptations of the above-described embodiments, implementations, and examples are encompassed by the attached claims.

The invention claimed is:

1. A method for evaluating a structure, the method comprising:
   illuminating a region of the structure with a beam, the structure having a plurality of lines passing through said region;
   generating an electrical signal indicative of an attribute of a portion of the beam, the portion being reflected from said region;
   repeating the acts of "illuminating" and "generating" in another region of the structure having another plurality of lines, thereby to obtain another electrical signal; and
   comparing said electrical signal with said another electrical signal to identify variation of a property in said region relative to said another region.

2. The method of claim 1 wherein:
   the attribute being measured is color.

3. The method of claim 1 wherein:
   the beam is nonpolarized;
   the attribute is a first intensity of a first component of said portion polarized in a direction substantially perpendicular to one of the lines, and the electrical signal is hereinafter "first electrical signal"; and
   the method further comprises generating a second electrical signal indicative of a second intensity of a second component of said portion polarized in a direction substantially parallel to said one of the lines.

4. A method for evaluating a structure, the method comprising: illuminating a region of the structure with a beam, the structure having a plurality of lines passing through said region;
   generating an electrical signal indicative of an attribute of a portion of the beam, the portion being reflected from said region;
   repeating the acts of "illuminating" and "generating" in another region having another plurality of lines, thereby to obtain another electrical signal; and
   comparing said electrical signal with said another electrical signal to identify variation of a property between said region and said another region;
   wherein the attribute being measured is color.

5. The method of claim 4 wherein:
   said region is at a predetermined location in the structure; and
   said another region is at said predetermined location in another structure.

6. The method of claim 4 wherein:
   said region is at a first location in the structure; and
   said another region is at a second location in said structure.

7. A method for evaluating a structure having at least a plurality of lines and a layer in contact with said lines, the method comprising:
   illuminating a region of the structure using a beam of electromagnetic radiation, the structure having a plurality of lines in said region, the beam having a wavelength greater than or equal to a pitch between at least two lines in the plurality, said two lines being each at least substantially parallel to and adjacent to the other; end
   generating an electrical signal indicative of color of a portion of the beam, the portion being reflected from said region.

8. The method of claim 7 wherein:
   the lines are conductive;
   the structure is a wafer having formed therein a plurality of integrated circuit dice; and
   the method further comprises changing a process parameter used in creation of another wafer based on the electrical signal.

9. The method of claim 7 further comprising:
   repeating the acts of "iiluminating" and "generating" in another region having another plurality of lines, thereby to obtain additional electrical signal for said another region; and
   comparing said electrical signal with said another electrical signal to identify variation of a material property between said region and said another region.

10. The method of claim 7 wherein:
    the attribute is a first color of a first component of said portion polarized in a direction perpendicular to one of the two lines, and the electrical signal is hereinafter "first electrical signal"; and
    the method further comprises generating a second electrical signal indicative of a second color of a second component of said portion polarized in a direction parallel to said one of the two lines.

11. The method of claim 10 wherein:
    the acts of generating are performed contemporaneously.

12. The method of claim 11 wherein:
    the lines are conductive;
    the structure is a wafer having formed therein a plurality of integrated circuit dice; and
    the method further comprises changing a process parameter used in creation of another wafer if the first electrical signal differs from the second electrical signal by a predetermined limit.

13. A method for evaluating a structure having at least a plurality of lines and a layer in contact with said lines, at least two lines in the plurality being each at least substantially parallel to the other, the method comprising:
    illuminating the structure with a beam of electromagnetic radiation having at least two polarized components wherein a first component is substantially parallel to the two lines, and a second component is substantially perpendicular to the two lines;
    generating a first electrical signal indicative of color of a portion of the first component reflected by at least said two lines; and
    generating a second electrical signal indicative of color of a portion of the second component reflected by the layer;
    wherein the acts of generating are performed at least contemporaneously relative to one another.

14. The method of claim 13 wherein:
the acts of generating are performed simultaneously relative to one another.

15. A method for evaluating a structure having at least a plurality of lines and a layer in contact with said lines, at least two lines in the plurality being each at least substantially parallel to the other, the method comprising:
illuminating a first region of the structure with a first beam of electromagnetic radiation;
illuminating a second region of the structure with a second beam of electromagnetic radiation;
generating a first electrical signal indicative of color of a portion of the first beam reflected from the first region;
generating a second electrical signal indicative of color of a portion of the second beam reflected from the second region; and
using a difference between the first electrical signal wit the second electrical signal as a profile of a surface in the structure.

16. The method of claim 15 wherein:
each of the first beam and the second beam is polarized; and
the first beam has a polarization direction perpendicular to the polarization direction of the second beam.

17. The method of claim 15 wherein:
each of the first beam and the second beam is polarized; and
the first beam has a polarization direction parallel to the polarization direction of the second beam.

18. The method of claim 15 wherein:
the lines are conductive;
the structure is a wafer having formed therein a plurality of integrated circuit dice; and
the method further comprises changing a process parameter used iii creation of another wafer if the first electrical signal differs from the second electrical signal by a predetermined limit.

19. An apparatus for evaluating a wafer having a plurality of lines, said apparatus comprising:
a source of a beam of electromagnetic radiation having a wavelength greater than or equal to a pitch between at least two lines in said wafer, said two lines being each at least substantially parallel to and adjacent to the other;
a camera that measures color located in a path of a portion of the bean, the portion being reflected from said region;
a memory; and
a comparator coupled to each of said memory and said camera.

20. The apparatus of claim 19 further comprising:
a polarizer located in a path of said beam between said source and said wafer.

21. The apparatus of claim 20 further comprising:
a stage supporting said wafer, the stage holding the wafer to orient the lines in a predetennined direction;
wherein the polarizer is aligned to orient polarization of the beam in said predetermined direction.

22. The apparatus of claim 20 further comprising:
a stage supporting said wafer, the stage holding the wafer to orient the lines in a predetermined direction;
wherein the polarizer is aligned to orient polarization of the beam perpendicular to said predetermined direction.

23. The apparatus of claim 19 wherein:
said memory is coupled to the camera; and
during operation, said memory stores a first signal generated by the camera at a first time, the first signal being related to a first region in the wafer and said comparator compares the first signal with a second signal generated by the camera at a second tine, the second signal being related to a second region.

24. An apparatus for evaluating a wafer having a plurality of lines, said apparatus comprising:
a source of abeam of electromagnetic radiation having a wavelength greater than or equal to a pitch between at least twa lines in said wafer, said two lines being each at least substantially parallel to and adjacent to the other;
a polarizing beam splitter located in a path of said beam between said source and said wafer; and
a polarizer located in a path of said beam between the polarizing beam splitter and the wafer.

25. The apparatus of claim 24 wherein:
the polarizing beam splitter is a Wollaston prism.

26. A method for evaluating a structure having at least a plurality of lines and a layer in contact with said lines, at least two lines in the plurality being each at least substantially parallel to the other, the method comprising:
polarizing a beam of white light to obtain a beam of polarized white light;
illuminating a region of the structure with said beam of polarized white light; and
measuring a color of a portion of said beam of polarized white light reflected from the region.

27. The method of claim 26 wherein:
the beam has a wavelength greater than a distance between center lines of the two lines.

28. The method of claim 27 wherein:
the beam is polarized in a direction substantially parallel to one of the two lines; and said portion is reflected by the two lines.

29. The method of claim 28 wherein:
the structure includes a layer located between a source of the beam and the two lines; and
the layer is at least partially transmissive, so tat said portion passes through the layer.

30. The method of claim 28 wherein said portion passes trough a trausmissive medium other than a layer of a semiconductor wafer, the transmissive medium being located between a source of the beam and the two lines.

31. The method of claim 28 wherein the beam is hereinafter "first beam ", the method further comprising:
illuminating said region with a second bean, a portion of energy in said second beam that is not reflected by said region being converted into heat, said second beam having an intensity modulated at a predetermined frequency being sufficiently small to cause a majority of said heat to transfer by diffusion from said region;
wherein the portion of the first beam sensed in the act of generating is modulated in phase with modulation of said second beam.

32. The method of claim 31 wherein:
the second beam is polarized in a direction parallel to one of the two lines; and at least a portion of the second beam reflects from a surface of said "one of the two lines".

33. The method of claim 27 wherein:
the beam polarized in a direction at least substantially perpendicular to one of the two lines;
the structure includes a layer located between the semiconductor substrate and the two traces; and
said portion is reflected by the layer.

34. The method of claim 33 wherein:
the lines are embedded within the layer so that at least a part of the layer is located between the two lines and at least some of said portion passes through said part.

35. The method of claim 33 wherein the beam contains photons having energy equal to or lower than bandgap energy of a semiconductor material in said region, the method further comprising:

creating a plurality of charge carriers in the layer, the charge carriers being modulated at a frequency that is sufficiently low to avoid creation of a wave of the charge carriers;

wherein the portion of the beam used in the act of generating is modulated at said frequency and in phase with modulation of the charge corners.

36. The method of claim 26 wherein the structure is a semiconductor wafer, the method further comprising, prior to the acts of illuminating and "generating":

adding dopant atoms to at least said region; and creating said plurality of lines in at least said region. the beam has a wavelength greater than a distance between center lines of the two lines.

37. The method of claim 36 further comprising:

changing a process parameter used in either one of the acts of adding and creating, if the variation is greater than a predetermined limit.

38. The method of claim 26 wherein said region is a first region and said color is a first color, the method further comprising:

illuminating a second region of the structure with said beam of polarized white light;

measuring a second color of a portion of said beam of polarized white light reflected from the second region; and using a difference in said first color and said second color to indicate a corresponding change in thickness of said layer.

39. The method of claim 26 wherein said measuring is performed by an optical instrument.

* * * * *